US010582995B2

(12) United States Patent
Gildener-Leapman et al.

(10) Patent No.: US 10,582,995 B2
(45) Date of Patent: Mar. 10, 2020

(54) INTRA-ORAL PROSTHESES AND OTHER ANATOMICAL PROSTHESES

(71) Applicant: University of Pittsburgh—Of the Commonwealth System of Higher Education, Pittsburgh, PA (US)

(72) Inventors: Neil Gildener-Leapman, Pittsburgh, PA (US); Youngjae Chun, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 767 days.

(21) Appl. No.: 15/121,311

(22) PCT Filed: Feb. 26, 2015

(86) PCT No.: PCT/US2015/017642
§ 371 (c)(1),
(2) Date: Aug. 24, 2016

(87) PCT Pub. No.: WO2015/130879
PCT Pub. Date: Sep. 3, 2015

(65) Prior Publication Data
US 2017/0014220 A1    Jan. 19, 2017

Related U.S. Application Data

(60) Provisional application No. 61/945,348, filed on Feb. 27, 2014.

(51) Int. Cl.
*A61F 2/02*      (2006.01)
*A61F 5/00*      (2006.01)
(Continued)

(52) U.S. Cl.
CPC ............ *A61F 2/02* (2013.01); *A61B 5/038* (2013.01); *A61B 5/4205* (2013.01);
(Continued)

(58) Field of Classification Search
CPC ...... A61F 2/02; A61F 2/08; A61F 2/50; A61F 2002/0894; A61F 2002/5066;
(Continued)

(56) References Cited

U.S. PATENT DOCUMENTS 4,471,771 A    9/1984   Steven et al.
5,052,409 A *  10/1991  Tepper .................... A61F 5/566
                                                  128/859
(Continued)

OTHER PUBLICATIONS

International Search Report and Written Opinion for related International Application No. PCT/US2015/017642, dated May 20, 2015, 10 pages.

*Primary Examiner* — Keri J Nelson
(74) *Attorney, Agent, or Firm* — Klarquist Sparkman, LLP

(57) ABSTRACT

Described herein are intra-oral prostheses that can help replace or augment the function of the native tongue, such as to assist with swallowing. Disclosed prostheses can provide mechanical force, based on the power of mastication, to propel a food bolus into the pharyngeal phase of swallowing. Disclosed prostheses can be used to enhance swallowing rehabilitation as a temporary aid and/or can be used to permanently replace lost tongue functionality. Also disclosed are other anatomical prostheses, such as to provide power for the articulation of dysfunctional extremities, by transforming mechanical force from another nearby functioning muscle group.

21 Claims, 21 Drawing Sheets

(51) Int. Cl.
*A61F 2/50* (2006.01)
*A61C 7/36* (2006.01)
*A61B 5/03* (2006.01)
*A61B 5/00* (2006.01)
*A61F 5/56* (2006.01)
*A61F 2/58* (2006.01)
*A61F 2/08* (2006.01)

(52) U.S. Cl.
CPC .............. *A61B 5/4851* (2013.01); *A61C 7/36* (2013.01); *A61F 2/50* (2013.01); *A61F 2/586* (2013.01); *A61F 5/0003* (2013.01); *A61F 5/566* (2013.01); *A61B 2505/09* (2013.01); *A61F 5/0006* (2013.01); *A61F 2002/0894* (2013.01); *A61F 2002/5066* (2013.01)

(58) Field of Classification Search
CPC ...... A61F 5/0003; A61F 5/0006; A61F 5/566; A61C 7/08; A61C 7/36
USPC .................................. 128/859–862; 433/140
See application file for complete search history.

(56) References Cited

U.S. PATENT DOCUMENTS

| | | |
|---|---|---|
| 7,934,506 B2 | 5/2011 | Woodson et al. |
| 8,381,735 B2 | 2/2013 | Buscemi et al. |
| 2011/0259346 A1 | 10/2011 | Tsuiki et al. |
| 2012/0109051 A1* | 5/2012 | Harrell .................. A61F 5/0006 604/77 |
| 2013/0255674 A1 | 10/2013 | Martin et al. |

* cited by examiner

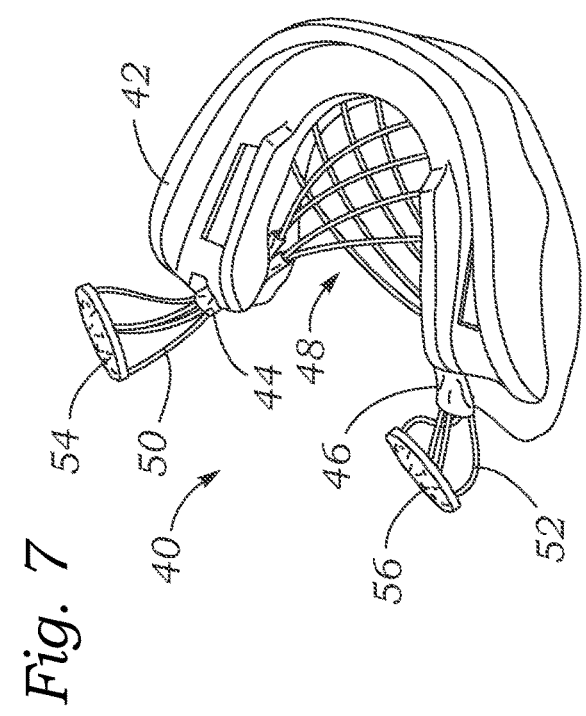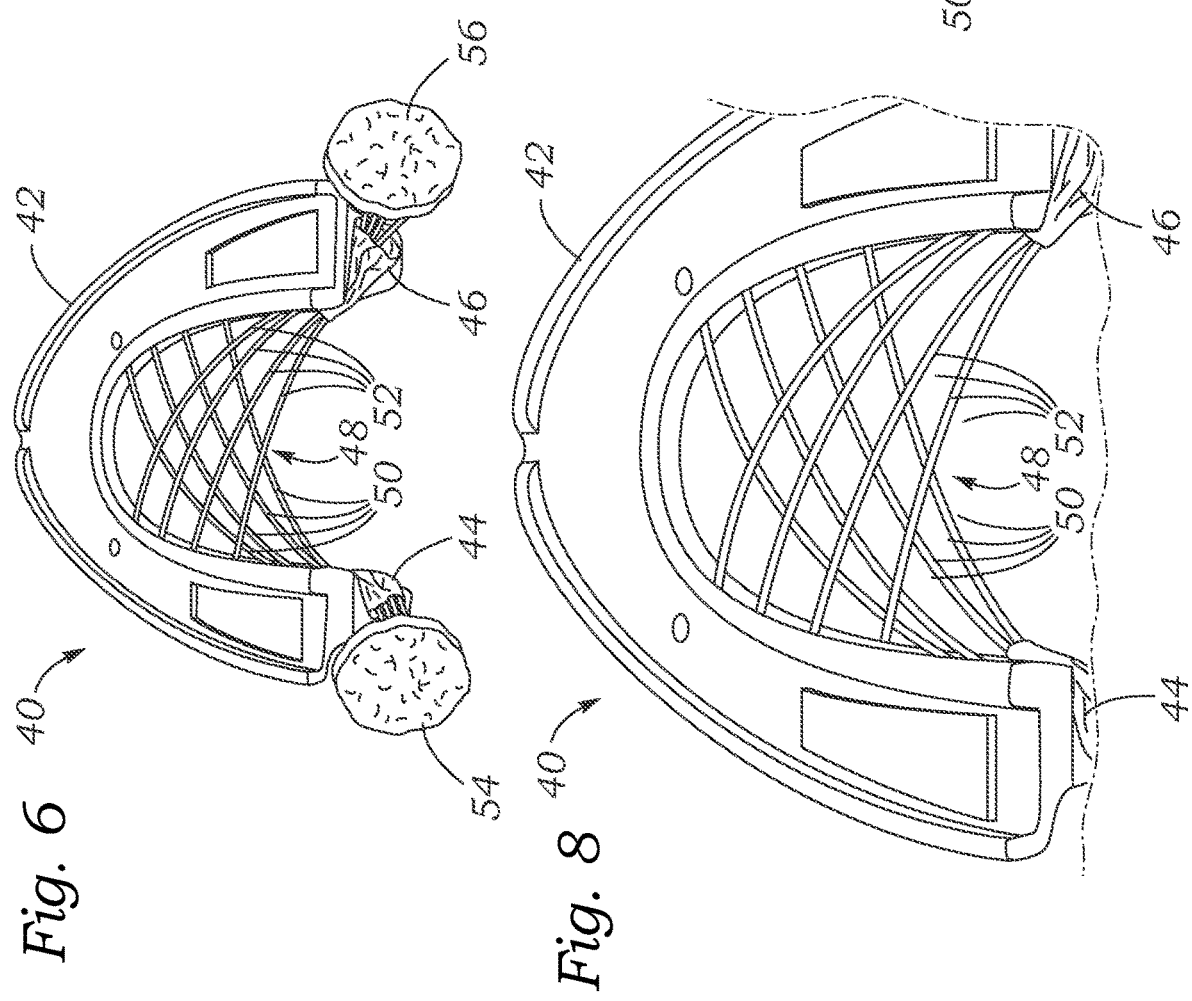

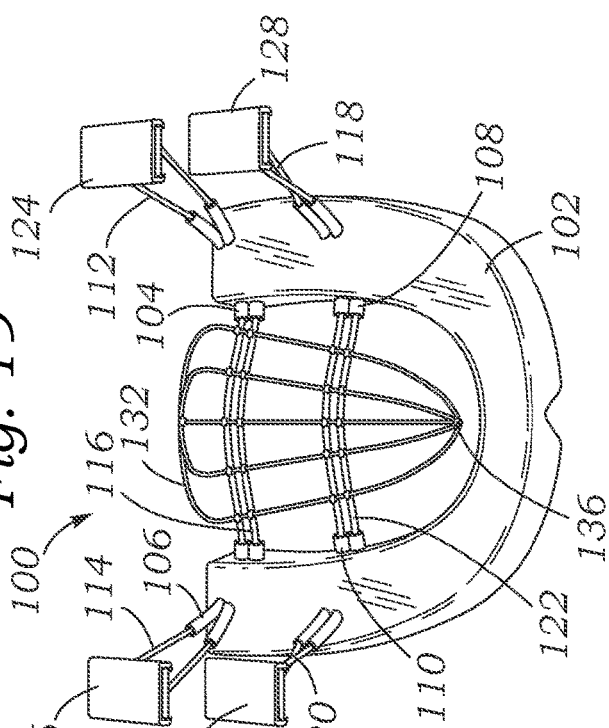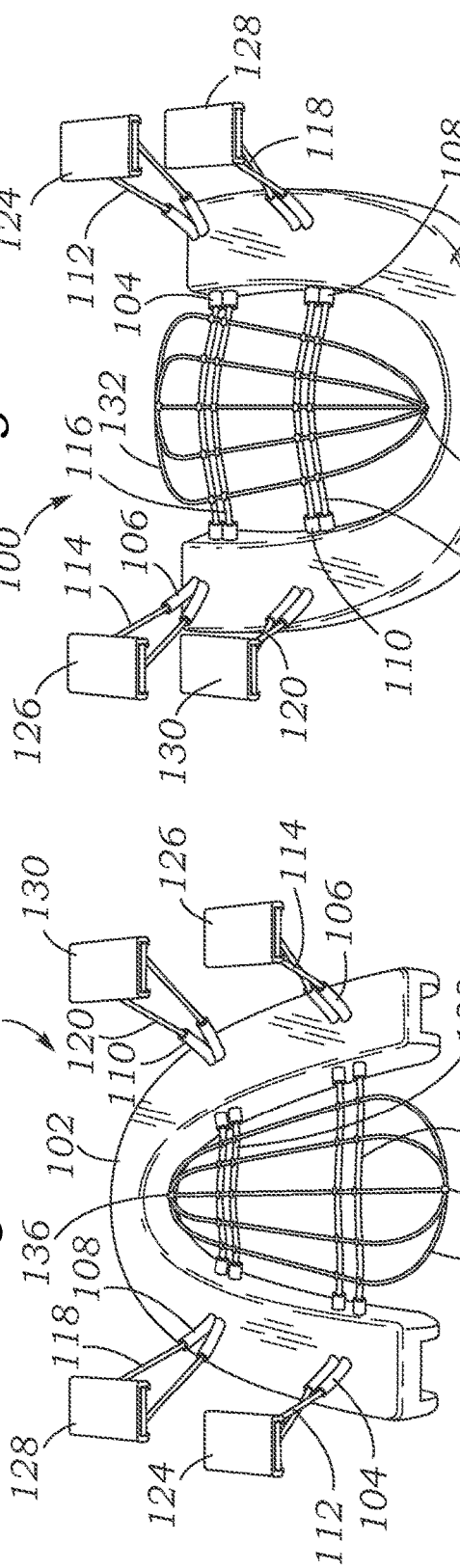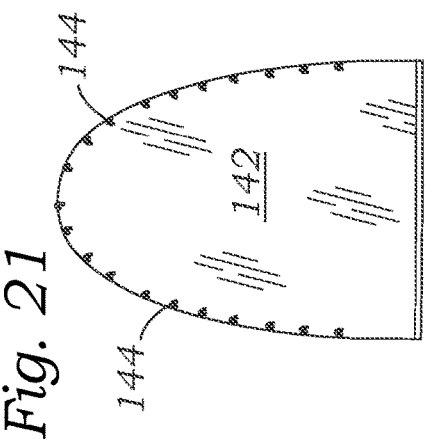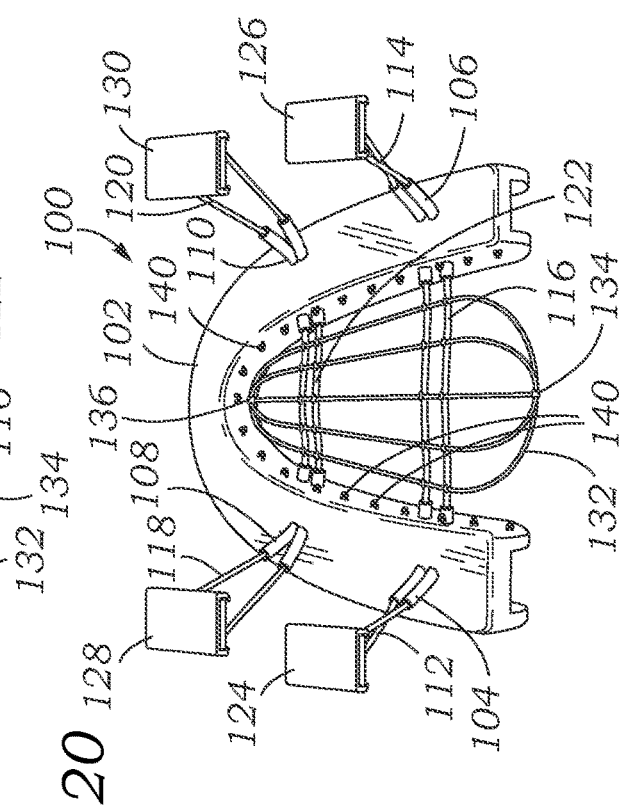

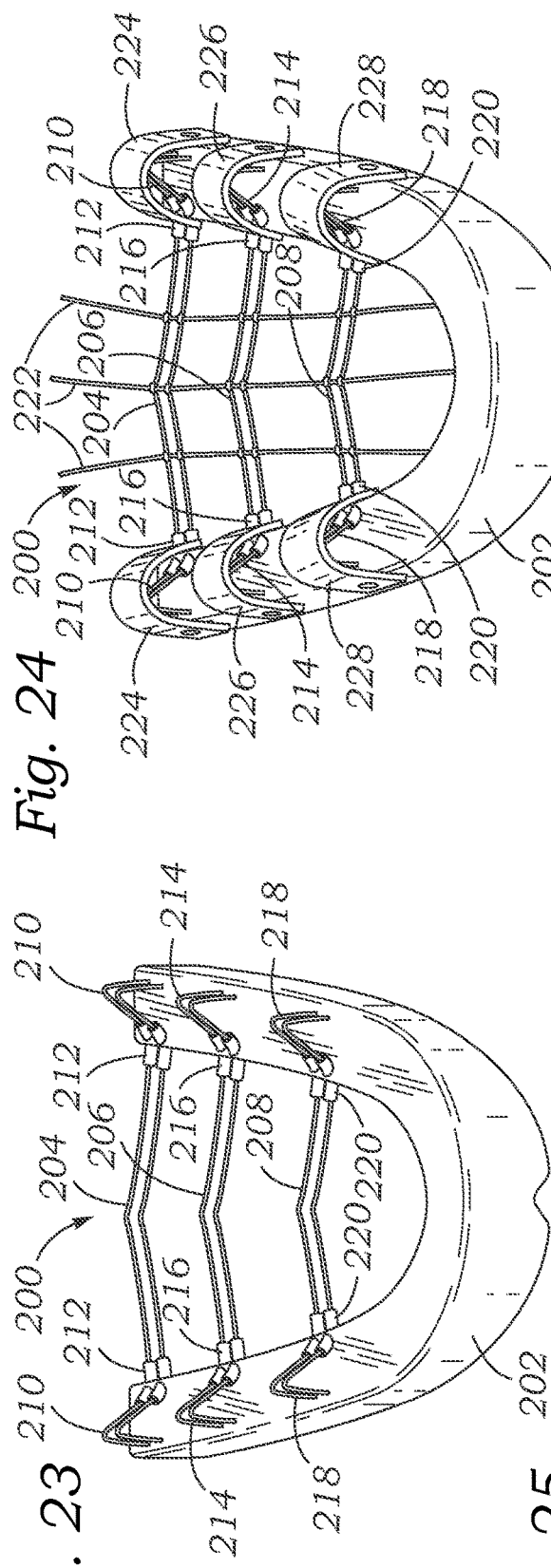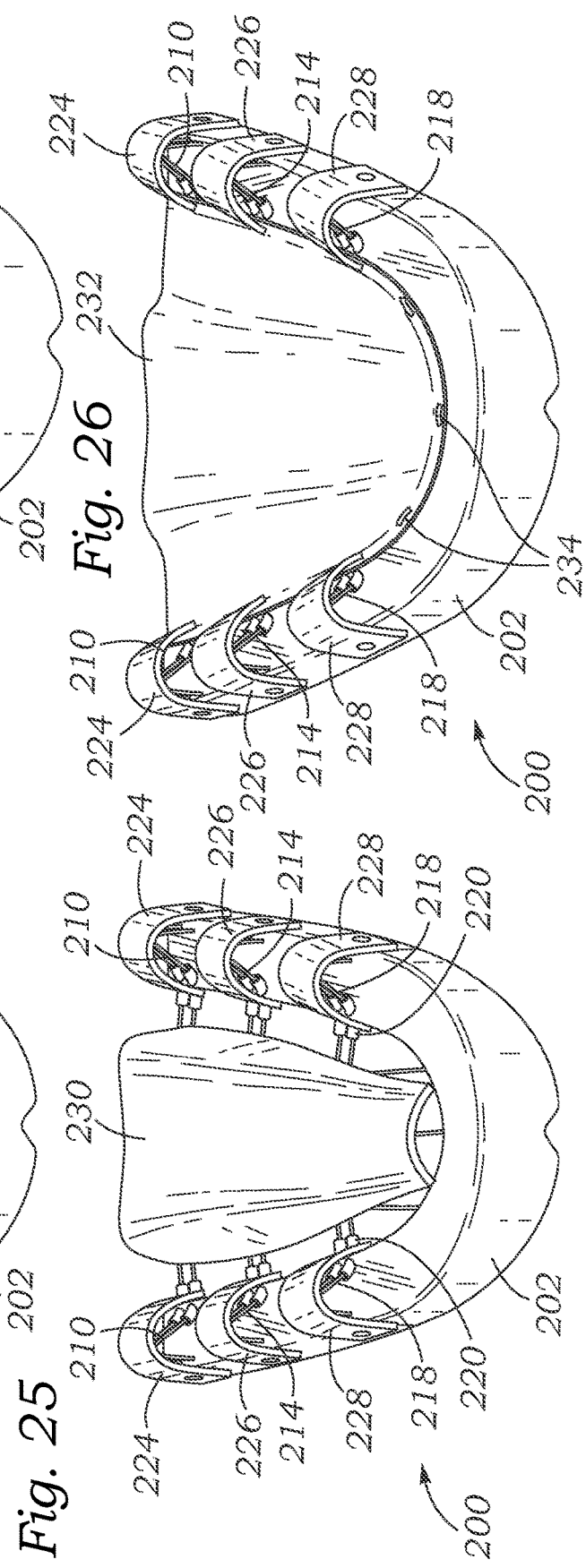

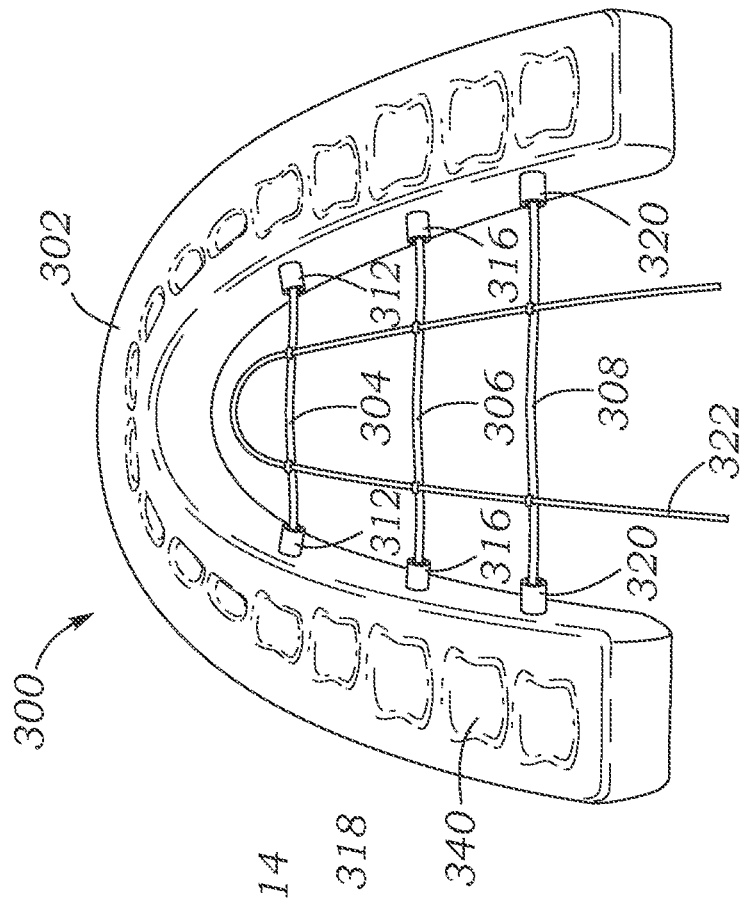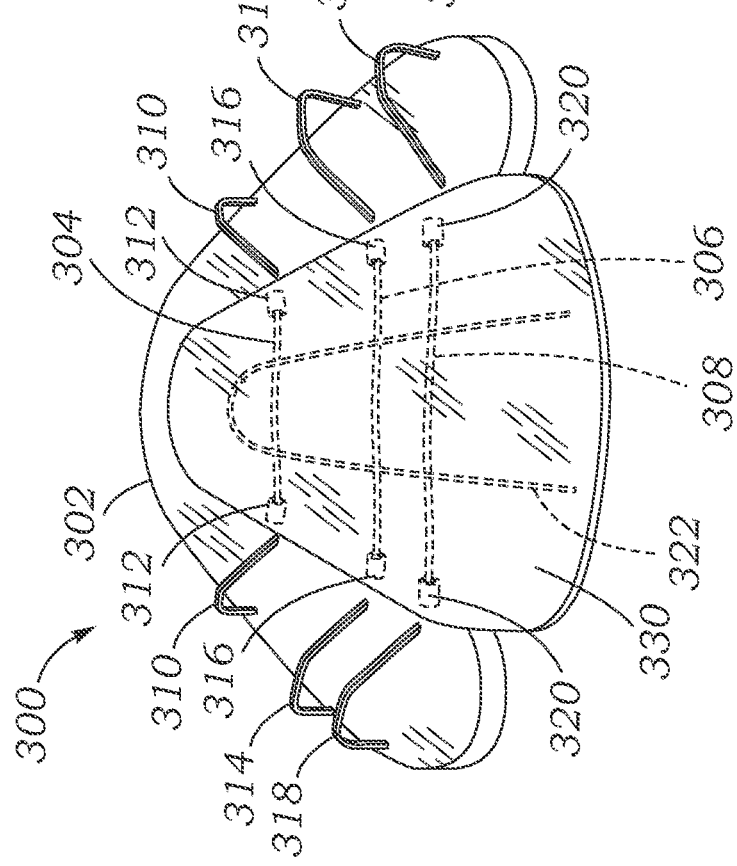

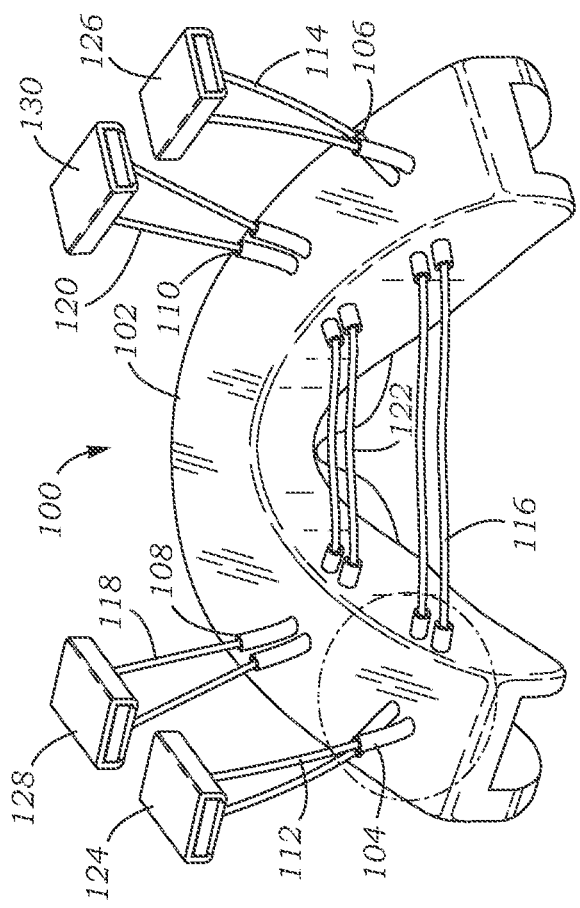

INTRA-ORAL PROSTHESES AND OTHER ANATOMICAL PROSTHESES

CROSS-REFERENCE TO RELATED APPLICATION

This application is the U.S. National Stage of International Application No. PCT/US2015/017642, filed Feb. 26, 2015, which claims the benefit of U.S. Provisional Patent Application No. 61/945,348, filed on Feb. 27, 2014, which is incorporated herein by reference in its entirety.

FIELD

This application is related to intra-oral prostheses, such as for treating dysphagia.

BACKGROUND

Millions of people require care for dysphagia, which often arises due to age, neurologic disease, radiation, or surgery, and can impair the ability to swallow. A subset of these patients have primarily oral or oropharyngeal based dysphagia, which affects up to 40% of patients 65 years or older. Some patients require supplemental feeding via a gastrostomy tube, which is accompanied by medical complications and may decrease quality of life. Much of the treatment for oropharyngeal dysphagia seeks to prevent complications such as aspiration pneumonia or malnutrition.

Current treatments for dysphagia include postural strategies for head or body position, change in food bolus volume or viscosity, tonic muscle contraction techniques such as neuromuscular electro-stimulation, specific swallow maneuvers, surgery, sensorial enhancement strategies, pharmacologic treatments, and gastrostomy tubes.

SUMMARY

Described herein are prosthetic intra-oral devices that can help replace or augment the function of the native tongue, such as to assist with swallowing. Disclosed prostheses can provide immediate mechanical force, based on the power of mastication, to propel the food bolus into the pharyngeal phase of swallowing. Disclosed devices can be used to enhance swallowing rehabilitation as a temporary aid and/or can be used to permanently replace lost tongue functionality.

Some disclosed intra-oral prostheses comprise a lower jaw portion configured to couple the prosthesis to a patient's lower jaw, for example at the lower dental arch, and a tongue portion coupled to the lower jaw portion. The tongue portion is comprised of a flexible portion configured to resiliently deform upwardly relative to the lower jaw portion toward the patient's upper jaw, e.g., the hard and soft palate, to simulate movement of the native tongue when the patient closes the jaws. The flexible portion of the tongue portion can comprise a lattice or mesh of superelastic wires, such as Nitinol wires.

The prostheses can include guide tubes fixed to, or formed in, the lower jaw portion, such that at least some of the wires extend through the guide tubes. The prostheses can also include an upper jaw portion configured to contact the patient's upper jaw, with the upper jaw portion being coupled to upper ends of the wires that extend through the guide tubes. When the patient articulates the lower jaw toward the upper jaw, the upper jaw portion of the prosthesis moves relatively toward the lower jaw portion of the device, which pushes the upper portions of the wires through the guide tubes and causes the tongue portion to bulge upwardly relative to the lower jaw portion.

Alternatively, in any iteration or embodiment of the disclosed intra-oral prostheses, the upper jaw portion may house the flexible tongue portion instead of or in addition to the lower jaw portion. The tongue portion may bulge downwardly from the upper jaw portion to contact and press on the native tongue or another object located where the native tongue usually is. In this way, the downwardly bulging tongue portion can effectively increase the pressure exerted on the food bolus. In some embodiments, the prosthesis can be specially manufactured to be positioned in the mouth with the tongue portion bulging down from the upper jaw portion, and in some embodiments, the prostheses can optionally be inserted into the mouth upside-down from the described orientation to cause the tongue portion to bulge downwardly from the upper jaw.

The tongue portion can include a sheet of flexible material that covers the resiliently deformable wires or strips and forms a continuous upper surface of the tongue portion. The sheet of material can be removably coupled to the lower jaw portion such that the sheet can be detached from the prosthesis and reattached to the prosthesis, such as for cleaning or replacement.

The upper jaw portion can comprises a single structure that extends around the upper teeth or gums, or can comprise at least two discrete upper jaw contact pads that contact the patient's upper jaw near the upper molars. Each of such contact pads can be attached to at least one of the superelastic wires.

The tongue portion can have an anterior elastic or superelastic deformation section and a posterior elastic or superelastic deformation section, and the anterior and posterior deformation sections can deform upwardly relative to the lower jaw portion independently of each other as the patient closes the patient's jaws.

The intra-oral prosthesis can also include at least one biasing member, such as springs, to bias the upper jaw portion apart from the lower jaw portion.

In some embodiments, the prosthesis can include flexible coils, such as helically coiled superelastic material, positioned around the wires that provide rigidity to the wires and help the wires move in a linear path into and through the guide tubes without buckling. The coils can extend through the guide tubes and provide a low friction interface with the guide tubes.

In some embodiments, at least some of the contact pads comprise a layer of flexible material, such as silicone, that arches over the second ends of the flexible wires and is secured to the lower jaw portion on the medial and lateral side, forming a low profile, more compact and sturdy prosthesis. In such embodiments, the lateral ends of the wires can form arches underneath the curved contact pads, with the lateral aspect of the wire arches being secured to the lower jaw portion and the medial aspect of the arches being slidable downwardly and medially through the guide tubes.

In some embodiments, the tongue portion can include a semi-rigid mass between the wires/wire lattice and the upper cover layer. Such a mass can add height to the tongue portion and can shape the tongue portion so better simulate a native tongue shape and function.

Also disclosed are non-oral anatomical prostheses that provide power for the articulation of dysfunctional extremities, such as the hands, feet, or digits, by transforming mechanical force from another nearby functioning muscle group to replace lost functionality of the dysfunctional extremities.

The foregoing and other objects, features, and advantages of the disclosed technology will become more apparent from the following detailed description, which proceeds with reference to the accompanying figures.

BRIEF DESCRIPTION OF THE DRAWINGS

FIG. 6 is a superior-anterior view of another exemplary intra-oral prosthesis.

FIG. 7 is a superior-lateral view of the intra-oral prosthesis of FIG. 6.

FIG. 8 is an enlarged view of a portion of FIG. 6.

FIG. 9 is an anterior view of the intra-oral prosthesis of FIG. 6

FIGS. 18 and 19 show an embodiment of the intra-oral prosthesis of FIG. 17 with a wire mesh tongue portion.

FIG. 20 shows an embodiment of the intra-oral prosthesis of FIG. 18 with loops for attaching a tongue cover over the wire mesh tongue portion.

FIG. 21 shows an exemplary tongue cover that can be attached to the intra-oral prosthesis of FIG. 20.

FIGS. 23-26 show another exemplary intra-oral prosthesis having three distinct bulging zones and arched upper jaw contacts. FIG. 25 shows a semi-rigid tongue portion that overlies the three bulging zones. FIG. 26 shows a cover layer that overlies the semi-rigid tongue portion and is coupled to the lower jaw portion.

FIGS. 27 and 28 show an embodiment similar to that shown in FIGS. 23-26, with FIG. 28 illustrating the lower surface of the lower jaw portion having been molded to a patient's teeth.

FIGS. 29A-29D illustrate exemplary testing parameters for testing the amount of resistance force that is created by various types of tubes passing through the lower jaw portion. The parameters include tube diameter, tube length, and tube bend angle.

DETAILED DESCRIPTION

Figure 1:
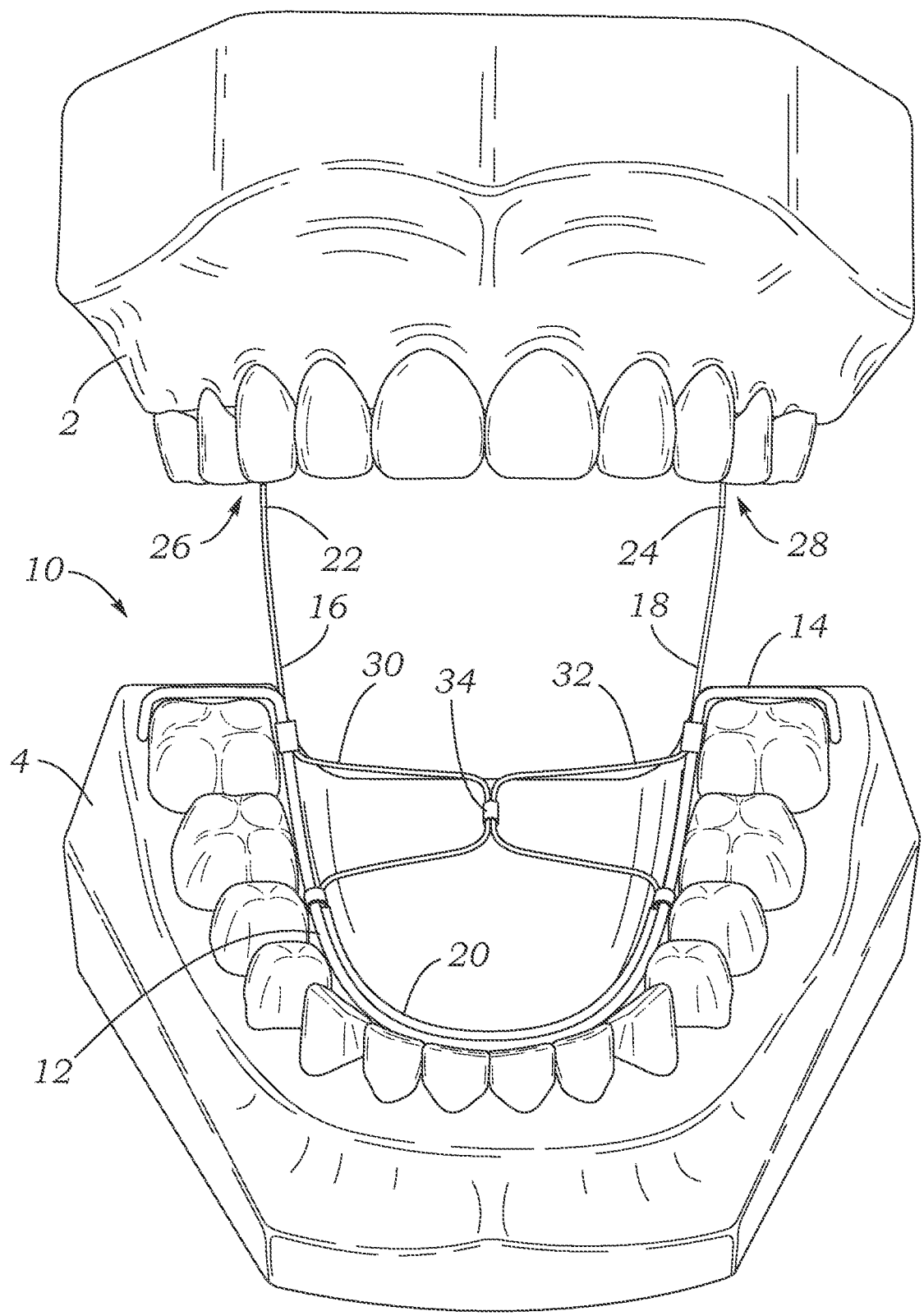
FIG. 1 shows an exemplary intra-oral prosthesis within a mouth with the lower jaw in a fully open position.
Figure 2:
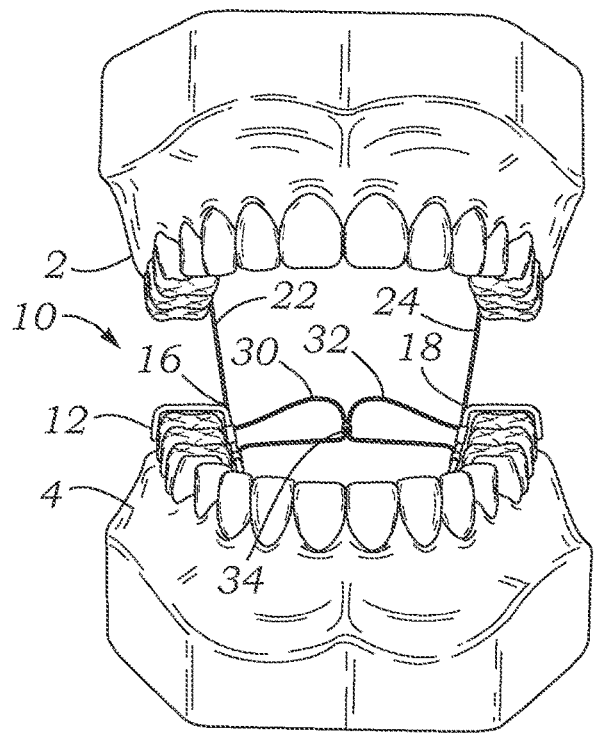
FIGS. 2-5 show the intra-oral prosthesis of FIG. 1 in various states of activation as the lower jaw gradually moves toward a closed position.
Figure 3:
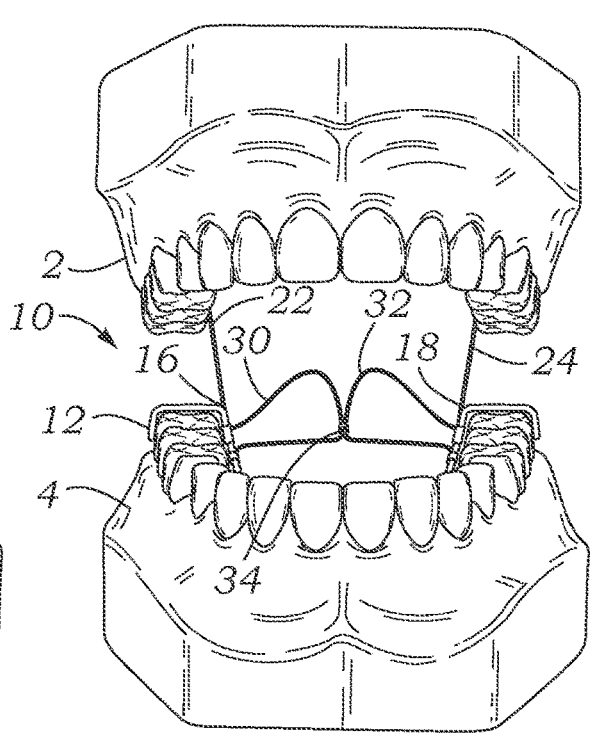
Figure 4:
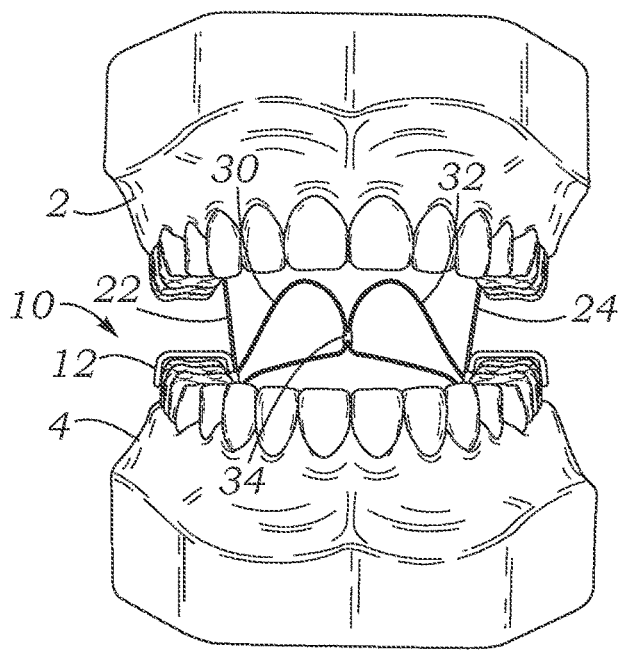
Figure 5:
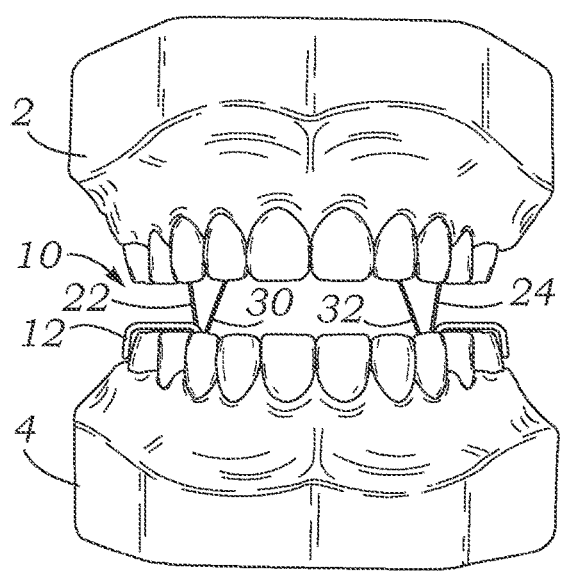

Described herein are examples of intra-oral prostheses that can help replace or augment the function of the native tongue, such as to the power and initiation of swallowing. The native tongue serves several functions, including helping to swallow, speaking, moving food around the mouth, tasting, and controlling breathing. When the native tongue is partially or completely removed, the patient may have difficulty with one or more of these functions.

During swallowing, the native tongue lifts up from the lower jaw and propels a food bolus from the mouth posteriorly into the pharyngeal phase of swallowing. The disclosed intra-oral prostheses can replace this tongue functionality by converting the power of the jaw-closing muscles to cause a prosthetic tongue portion to rise upwardly from the lower jaw toward the palate or oropharynx to simulate the native tongue motion during swallowing.

Alternatively, in some embodiments of intra-oral prostheses, the upper jaw portion can house the flexible tongue portion instead the lower jaw portion. The tongue portion, housed by the upper jaw portion, may bulge downwardly from the upper jaw portion to contact and press on the native tongue or another object located where the native tongue usually is. In this way, the downwardly bulging tongue portion can effectively increase the pressure exerted on the food bolus. In some embodiments, prostheses can be specially manufactured to be positioned in the mouth with the tongue portion bulging downward from the upper jaw portion, and in some embodiments, the prostheses can optionally be inserted into the mouth with the tongue portion adjacent the lower jaw, as described herein, or in an orientation upside-down from the described orientations, to cause the tongue portion to be located adjacent the upper jaw and bulge downwardly from the upper jaw. It should be understood that any of the embodiments described herein can be used as described with the tongue portion bulging up or in an inverted configuration with the tongue portion bulging down, unless non-practical or otherwise noted.

FIGS. 1-5 show an exemplary intra-oral prosthesis 10 positioned between an upper jaw 2 and a lower jaw 4 of a mouth that is missing a tongue. The prosthesis 10 comprises a lower jaw portion, or anchor portion, 12 that couples or anchors the prosthesis to the lower jaw 4, such as at the lower dental arch. The lower jaw portion 12 can comprise a denture, framework, dental appliance, or U-shaped channel that conforms to the lower dental arch, or other supporting structure 14 that mounts around the lower teeth and gums and/or at an area of the lower jaw 4 around where the native tongue is usually located. The lower jaw portion 12 can be secured to the lower jaw 4, such as with an adhesive or friction fit, and can be removable from the lower jaw to allow the patient to readily insert and remove the prosthesis 10 as needed.

The prosthesis 10 further comprises a tongue portion 34 that is formed by a plurality of flexible wires, such as wires 30 and 32, and that is configured to bulge upwardly and/or posteriorly relative to the lower jaw portion 12 when the lower jaw 4 closes upwardly toward the upper jaw 2, in order to simulate the native tongue motion during swallowing. In other embodiments, the tongue portion can bulge downwardly from an anchor portion anchored to the upper jaw, such that the tongue portion presses against or cooperates with the native tongue or a prosthetic tongue to help shape and propel a fool bolus posteriorly.

With respect the illustrated embodiments, the tongue portion may be situated over the native tongue in cases where the native tongue is still present in the mouth but may be too weak or otherwise impaired in functionality. The wires 30, 32 can comprise a superelastic material, such as Nitinol or similar metal alloys, which allows the wires to be pre-formed in a desired shape and helps control the deformation properties of the wires during articulation of the jaw. For example, the wires can be formed into the desired shapes by applying a mechanical shape setting process, such as a stress-induced martensitic transformation. In the example shown in FIG. 1, the two wires 30, 32 are curved toward each other and attached together at a central area of the tongue portion 34 such that they buckle/bulge upward when the jaw is closed.

The tongue portion 34 shown in FIGS. 1-5 is a straightforward example, while in other embodiments the tongue portion can include more wires and/or more complex lattice or mesh configurations of the wires. The tongue portion can be covered with a flexible layer of material, such a polymeric sheet, which provides a solid surface to the top of the tongue portion to better assist in moving a food bolus posteriorly. Such a sheet or layer can be removable and re-attachable to the lower jaw portion or to the tongue portion to allow the patient to replace it and/or clean the prosthesis.

The wires 30, 32 can be attached at one end to lower jaw portion 12, such as at anterior portion 20 (FIG. 1), while the opposite ends of the wires are coupled to an actuation portion, such as in contact with the upper jaw 2. As shown in FIGS. 1-5, for example, the wire 30 comprises an upper end 22 that terminates at a first upper jaw contact 26 and the wire 32 comprises an upper end 24 that terminates at a second upper jaw contact 28. The upper jaw contacts 26, 28 engage with the patient's upper jaw 2, such as with the upper teeth, gums, and/or with tissue of the hard or soft palate. The upper jaw contacts 26, 28 can comprise individual pads located on opposite sides of the upper jaw 2, or can comprise a single denture or other structure that extends around the upper jaw 2 following the upper teeth or gums. As the lower jaw 4 closes and moves the lower jaw portion 12 toward the upper jaw contacts 26, 28, compressive forces are applied to the upper ends 22, 24 of the wires, which cause the tongue portion 34 to bulge upwardly relative to the lower jaw 4.

The intra-oral prosthesis can further comprise guides that are part of, or are secured to, the lower jaw portion 12 to guide the path of the wires 30, 32 as the lower jaw 4 closes and opens. As shown in FIGS. 1-5, the prosthesis 10 can comprise guide tubes 16, 18 that are secured to the lower jaw portion 12 below the upper jaw contacts 26, 28. The wires 30, 32 are routed through the guide tubes 16, 18 such that the guide tubes can control the path of the wires as the jaw closes. The guide tubes can comprise a low friction material, such as a polymeric or metallic material, that allows the wires to slide through the tubes with minimal friction. The guide tubes can be oriented in a curved path to cause the wires to deform along the curved path as the wires are pushed through the tubes. When the jaw closes, the upper ends 22, 24 of the wires move toward and through the guide tubes 16, 18 such that more of the wires 30, 32 become located between the guide tubes in the tongue portion 34, causing the tongue portion to bulge upward.

FIGS. 6-9 show another exemplary intra-oral prosthetic 40 comprising a lower jaw portion, or anchor portion, 42 that couples the prosthesis to the lower dental arch. The lower jaw portion 12 can comprise a denture or other supporting structure that mounts around the lower teeth, gums, and/or at an area of the lower jaw around where the native tongue is usually located. The lower jaw portion 42 can be secured to the lower jaw, such as with an adhesive or friction fit, and can be removable from the lower jaw to allow the patient to readily insert and remove the prosthesis 40 as needed.

The prosthesis 40 further comprises a tongue portion 48 that is formed by a plurality of flexible wires 50, 52 and that is configured to bulge upwardly and/or posteriorly from the lower jaw portion 42 when the lower jaw closes upwardly toward the upper jaw, in order to simulate the native tongue motion during swallowing. In other embodiments, the tongue portion can bulge downwardly from an anchor portion anchored to the upper jaw, such that the tongue portion presses against or cooperates with the native tongue or a prosthetic tongue to help shape and propel a fool bolus posteriorly.

The wires 50, 52 can comprise a superelastic material, such as Nitinol or similar metal alloys, which allows the wires to be pre-formed in a desired shape and helps control the deformation properties of the wires during articulation of the jaw. The tongue portion 48 comprises a lattice configuration of the wires 50 and 52, as shown in FIG. 8. The wires 50 extend from the left-posterior of the lower jaw portion 42 toward attachment points at the right-anterior of the lower jaw portion. Conversely, the wires 52 extend from the right-posterior of the lower jaw portion 42 toward attachment points at the left-anterior of the lower jaw portion. The wires 50 can be woven with the wires 52, as shown, to form a latticework tongue portion 48 that deforms as a unit to provide a three-dimensional, rounded upward bulging when the jaw is closed.

The tongue portion can be covered with a flexible layer of material, such a polymeric sheet, which provides a solid surface to the top of the tongue portion to better assist in moving a food bolus posteriorly. Such a sheet or layer can be removable and re-attachable to the lower jaw portion 42 or to the tongue portion 48 to allow the patient to replace it and/or clean the prosthesis.

The wires 50, 52 can be attached at one end to the lower jaw portion 42, as shown in FIG. 8, while the opposite ends of the wires 50, 52 are coupled to actuation portions, such as left and right upper jaw contacts 54, 56, respectively. As shown in FIGS. 7 and 9, for example, the upper ends of the four wires 50 terminate at a first upper jaw contact 54, and the upper ends of the four wires 52 terminate at a second upper jaw contact 56. The upper jaw contacts 54, 56 engage with the patient's upper jaw, such as with the upper teeth and/or with tissue of the hard or soft palate. The upper jaw contacts 54, 56 can comprise individual pads located on opposite sides of the upper jaw. As the lower jaw closes and moves the lower jaw portion 42 toward the upper jaw contacts 54, 56, compressive forces are applied to the wires 50, 52, which cause the tongue portion 48 to bulge upwardly relative to the lower jaw portion 42.

As shown in FIGS. 6-9, the prosthesis 40 can comprise guide tubes 44, 46 that are secured to, or pass through, the lower jaw portion 42 below the upper jaw contacts 54, 56. The wires 50, 52 are routed through the guide tubes 44, 46 such that the guide tubes can control the path of the wires as the jaw closes. In some embodiments, two or more wires can pass through each guide tube. The guide tubes can comprise a low friction material, such as a polymeric or metallic material, that allows the wires to slide through the tubes with minimal friction. The guide tubes can be oriented in a curved path to cause the wires to deform along the curved path as the wires are pushed through the tubes. When the patient's jaw closes, the upper jaw contacts 54, 56 push the wires 50, 52 down through the guide tubes 44, 46 such that a larger portion of the wires become located in the tongue portion 48, causing the tongue portion to bulge upward relative to the lower jaw portion 42.

FIGS. 10-13 show another exemplary intra-oral prosthesis 60 that is similar to the prosthesis 40. The prosthesis 60 comprises a lower jaw portion 62 that couples the prosthesis to the lower dental arch. The lower jaw portion 62 can comprise a denture or other supporting structure that mounts around the lower teeth and/or at an area of the lower jaw around where the native tongue is usually located. The lower jaw portion 62 can be secured to the lower jaw, such as with an adhesive or friction fit, and can be removable from the lower jaw to allow the patient to readily insert and remove the prosthesis 60 as needed.

The prosthesis 60 further comprises a tongue portion 68 that is formed by a plurality of flexible wires 70, 72 and that is configured to bulge upwardly and/or posteriorly from the lower jaw portion 62 when the lower jaw closes upwardly toward the upper jaw, in order to simulate the native tongue motion during swallowing. In other embodiments, the tongue portion can bulge downwardly from an anchor portion anchored to the upper jaw, such that the tongue portion presses against or cooperates with the native tongue or a prosthetic tongue to help shape and propel a fool bolus posteriorly.

The wires 70, 72 can comprise a superelastic material, such as Nitinol or similar metal alloys, which allows the wires to be pre-formed in a desired shape and helps control the deformation properties of the wires during articulation of the jaw. The tongue portion 68 comprises a lattice formed of the wires 50 interwoven with the wires 52. The wires 70 extend from the left-posterior of the lower jaw portion 62 toward attachment points at the right-anterior of the lower jaw portion. Conversely, the wires 72 extend from the right-posterior of the lower jaw portion 62 toward attachment points at the left-anterior of the lower jaw portion. The wires 70 can be woven or otherwise engaged with the wires 72, as shown, to form a unified tongue portion 68 that provides a three-dimensional, rounded upward bulging when the jaw is closed.

The tongue portion 68 can be covered with a flexible layer of material, such a polymeric sheet, which provides a solid surface to the top of the tongue portion to better assist in moving a food bolus posteriorly. Such a sheet or layer can be removable and re-attachable to the lower jaw portion 62 or to the tongue portion 68 to allow the patient to replace it and/or clean the prosthesis.

Figure 10:
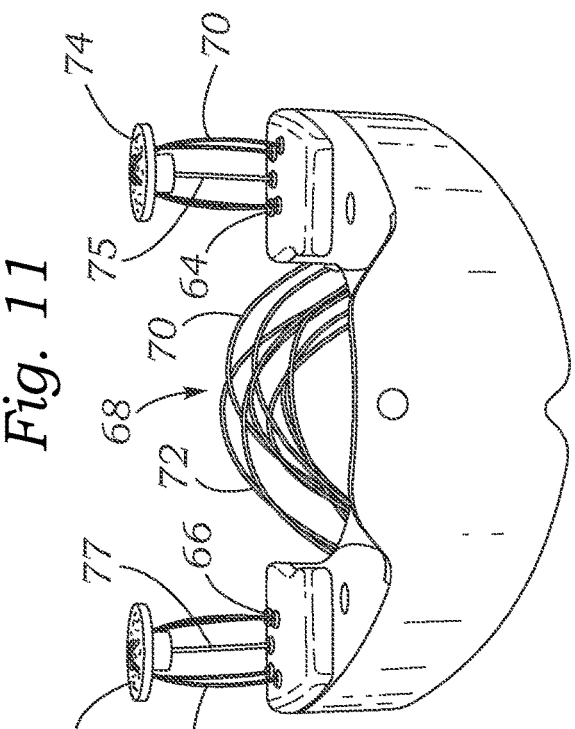
FIG. 10 is an anterior view of another exemplary intra-oral prosthesis in a relaxed state.
Figure 12:
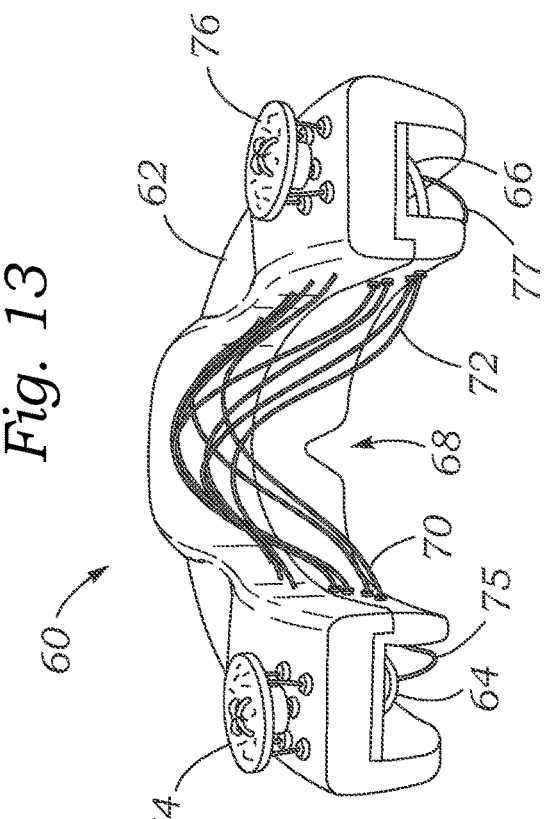
FIG. 12 is a posterior view of the intra-oral prosthesis of FIG. 10 in the relaxed state.

The wires 70, 72 can be attached at one end to the lower jaw portion 62, as shown in FIG. 12, while the opposite ends of the wires are coupled to left and right upper jaw contacts 74, 76, respectively. As shown in FIGS. 10 and 12, for example, the upper ends of the four wires 70 terminate at a left upper jaw contact 74, and the upper ends of the four wires 72 terminate at a right upper jaw contact 76. The upper jaw contacts 74, 76 engage with the patient's upper jaw, such as with the upper teeth and/or with tissue of the palate. The upper jaw contacts 74, 76 can comprise individual pads located on opposite sides of the upper jaw. As the lower jaw closes and moves the lower jaw portion 62 toward the upper jaw contacts 74, 76, compressive forces are applied to the wires 70, 72, which cause the tongue portion 68 to bulge upwardly relative to the lower jaw portion 62. As the upper jaw contacts 74, 76 are pushed toward the lower jaw portion 62, wires 75, 77 extending from the bottom of the upper jaw contacts slide down through/into the lower jaw portion and guide the travel path of the upper jaw contacts and/or provide a spring force that acts to push the upper jaw contacts back up when the user opens his jaws.

Figure 11:
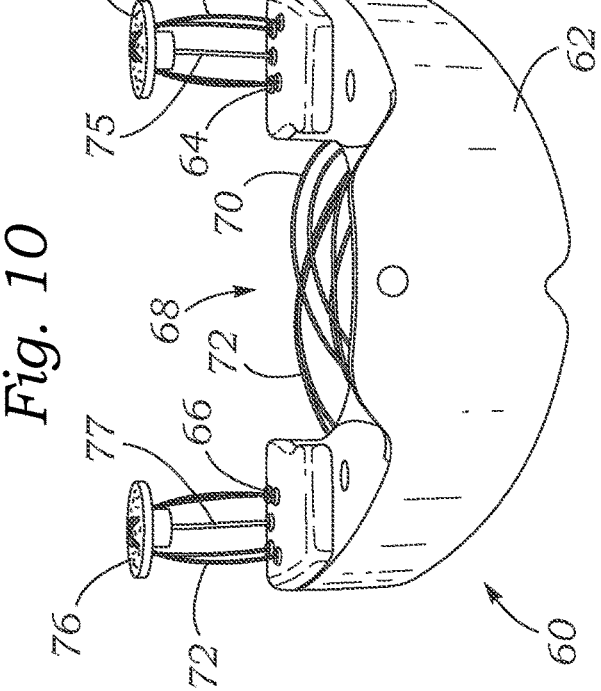
FIG. 11 is an anterior view of the intra-oral prosthesis of FIG. 10 in an activated state.
Figure 13:
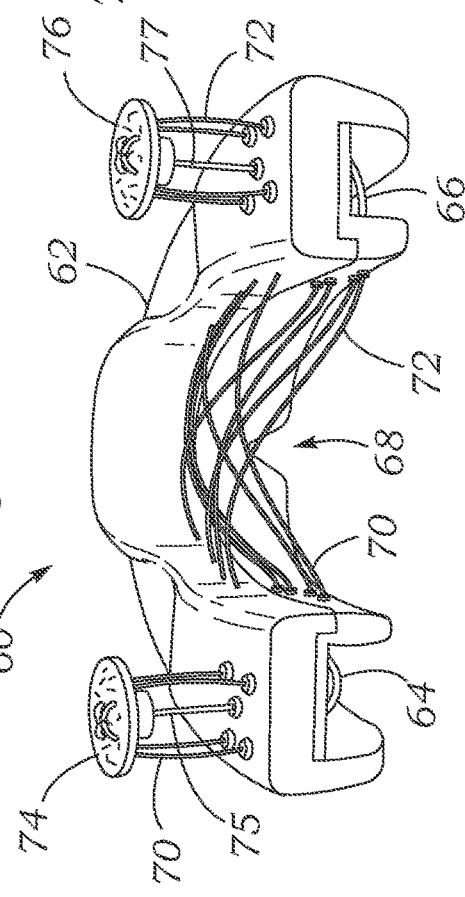
FIG. 13 is a posterior view of the intra-oral prosthesis of FIG. 10 in the activated state.

As shown in FIGS. 10-13, the prosthesis 60 can also comprise guide tubes 64, 66 that are secured to, or pass through, the lower jaw portion 62 below the upper jaw contacts 74, 76. The wires 70, 72 are routed through the guide tubes 74, 76 such that the guide tubes can control the path of the wires as the jaw closes. As shown, each wire passes through an individual guide tube, though in other embodiments, two or more wires can pass through some or all of the guide tubes. The guide tubes 64, 66 can comprise a low friction material, such as a polymeric or metallic material, that allows the wires to slide through the tubes with minimal friction. The guide tubes can be oriented in a curved path to cause the wires to deform along the curved path as the wires are pushed through the tubes. FIGS. 10 and 12 show the prosthesis 60 in an unactuated state, such as when the patient's jaw is open. When the patient's jaw closes, the upper jaw contacts 74, 76 push the wires 70, 72 down through the guide tubes 64, 66 such that a larger portion of the wires become located in the tongue portion 68, causing the tongue portion to bulge upward relative to the lower jaw portion 62, as shown in FIGS. 11 and 13.

Figure 14:
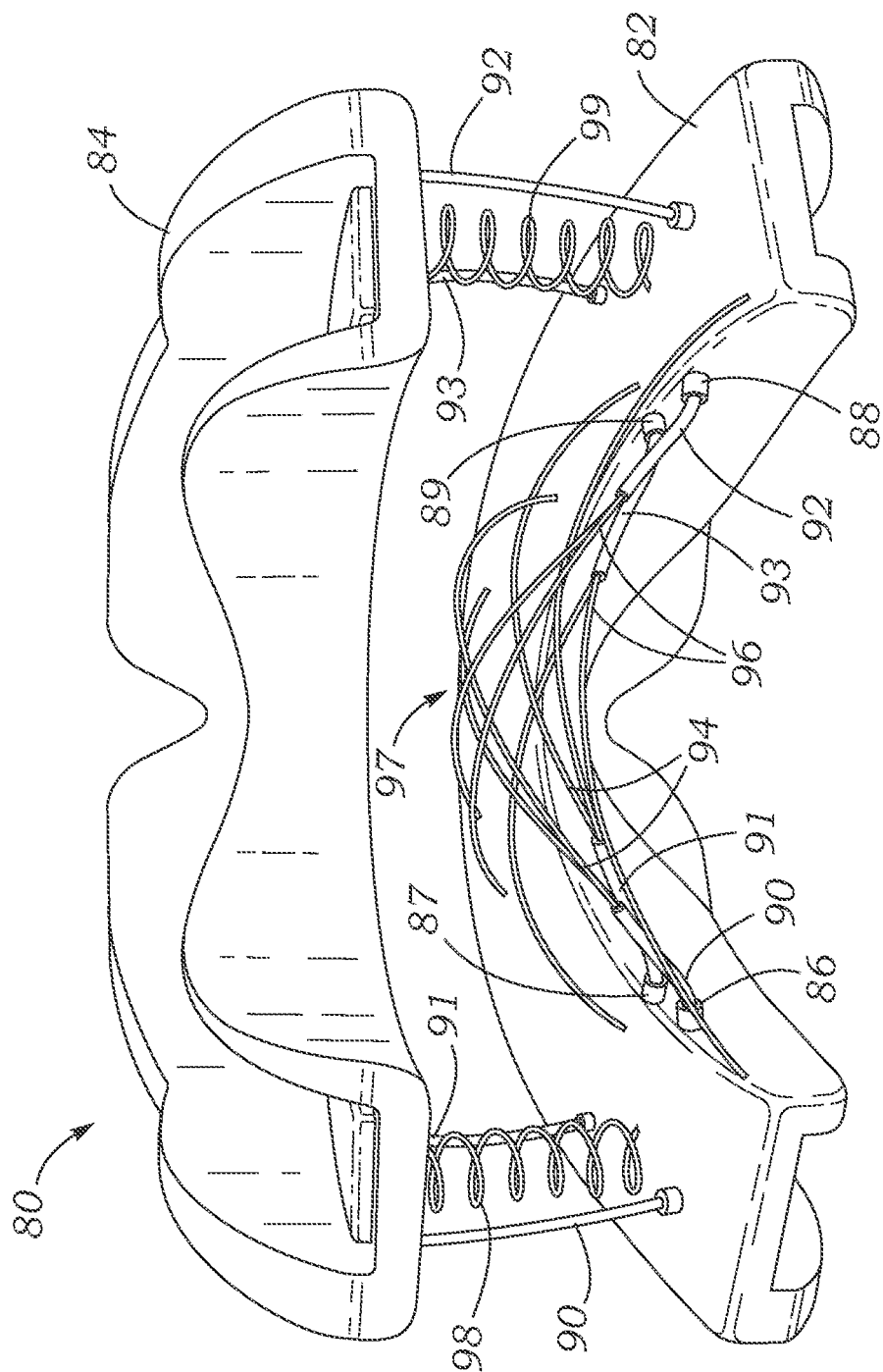
FIG. 14 is a posterior view of another intra-oral prosthesis.
Figure 15:
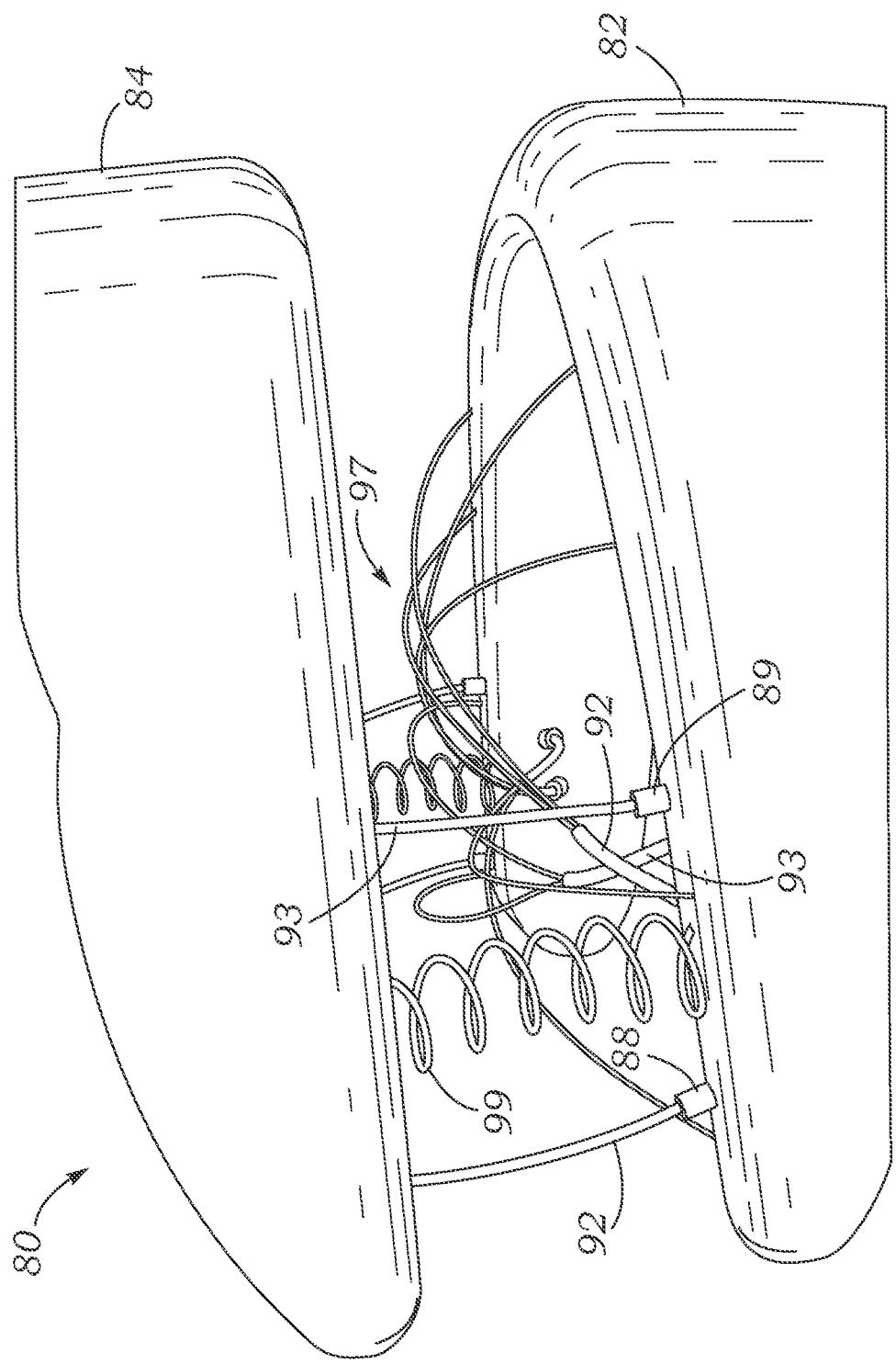
FIG. 15 is a lateral view of the intra-oral prosthesis of FIG. 14.
Figure 16:
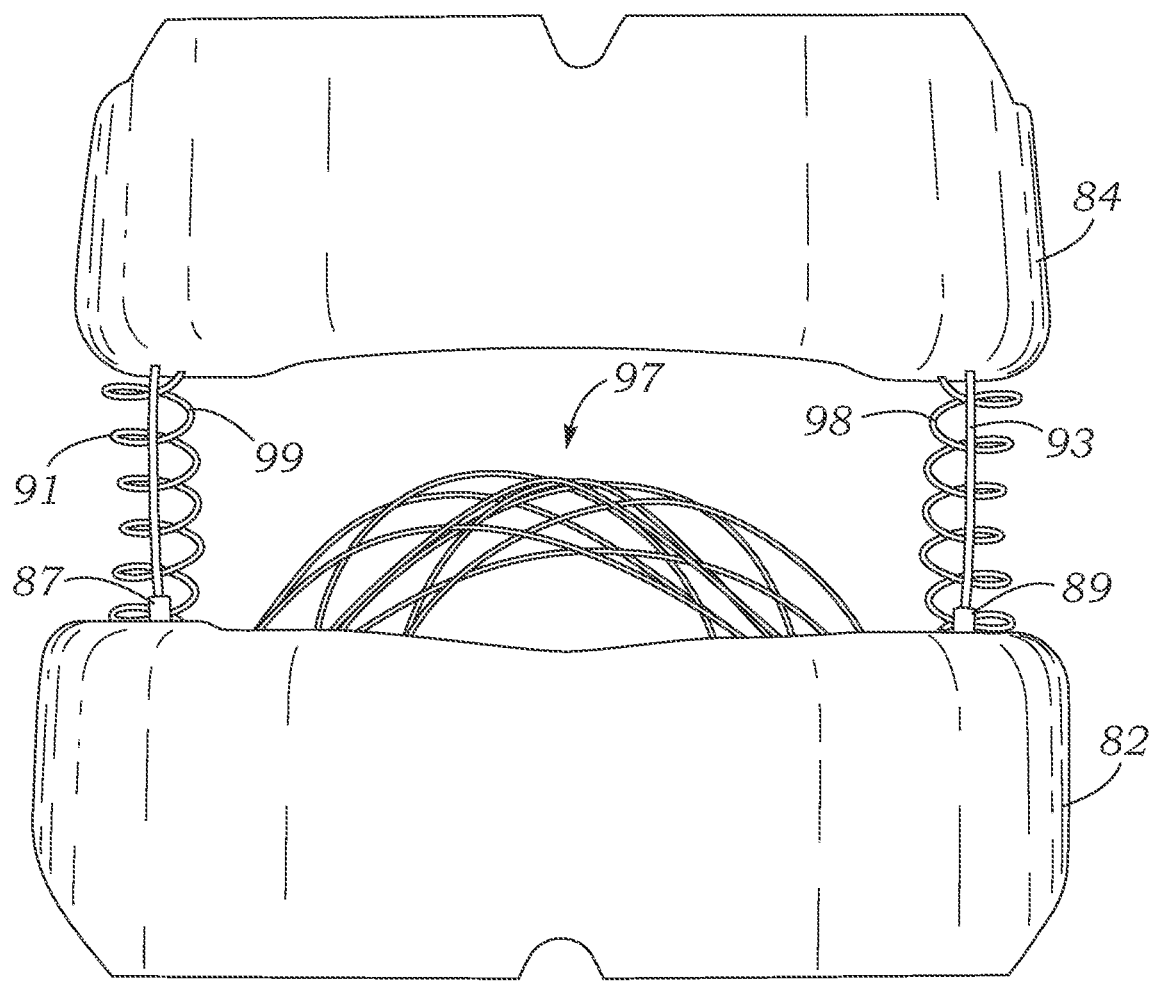
FIG. 16 is an anterior view of the intra-oral prosthesis of FIG. 14.

FIGS. 14-16 show another exemplary intra-oral prosthesis 80 that comprises a lower jaw portion 82 that couples the prosthesis to the patient's lower dental arch, and an opposing upper jaw portion 84 that couples the prosthesis to the patient's upper dental arch. The lower and upper jaw portions 82, 84 can comprise dentures or other supporting structures that mount around the teeth, gums, and/or at an area where the teeth are usually located. The jaw portions 82, 84 can be detachably secured to the patient's jaw, such as with an adhesive or friction fits, such that the patient can readily insert and remove the prosthesis 80 as needed.

The upper and lower jaw portions 82, 84 are coupled together by a biasing mechanism that biases the upper and lower jaw portions apart from each other, such that they stay with the jaws and spread apart when the patient's mouth opens. The biasing mechanism can comprise one or more springs, such as left and right coil springs 98, 99 as shown, linear springs, leaf springs, etc. The biasing mechanism can alternatively comprise other structures, such as a hinged joint between the left and right posterior ends of the upper and lower jaw portions 82, 84. The upper and lower jaw portions 82, 84 can be combined as a unitary structure that is connected at the left and right posterior ends, near the molars.

The prosthesis 80 further comprises a tongue portion 97 that is formed by a plurality of flexible wires 94, 96 and that is configured to bulge upwardly and/or posteriorly from the lower jaw portion 82 when the lower jaw closes upwardly toward the upper jaw, in order to simulate the native tongue motion during swallowing. In other embodiments, the tongue portion can bulge downwardly from the upper jaw portion 84 that is anchored to the upper jaw, such that the tongue portion presses against or cooperates with the native tongue or a prosthetic tongue to help shape and propel a fool bolus posteriorly.

The wires 94, 96 can comprise a superelastic material, such as Nitinol or similar metal alloys, which allows the wires to be pre-formed in a desired shape and helps control the deformation properties of the wires during articulation of the jaw. The tongue portion 97 comprises a lattice formed of the wires 94 interwoven with the wires 96. The wires 97 extend from the left-posterior of the lower jaw portion 82 toward attachment points at the right-anterior of the lower jaw portion. Conversely, the wires 96 extend from the right-posterior of the lower jaw portion 82 toward attachment points at the left-anterior of the lower jaw portion. The wires 94 can be woven or otherwise engaged with the wires 96, as shown, to form a unified tongue portion 97 that provides a three-dimensional, rounded, upward bulge when the jaw is closed.

The tongue portion 97 can be covered with a flexible layer of material, such a polymeric sheet, which provides a solid surface to the top of the tongue portion to better assist in moving a food bolus posteriorly. Such a sheet or layer can be removable and re-attachable to the lower jaw portion 82 or to the tongue portion 97 to allow the patient to replace it and/or clean the prosthesis.

The wires 94, 96 can be attached at one end to the lower jaw portion 82, as shown in FIG. 14, while the opposite ends of the wires are coupled to an actuation portion opposite from the anchor portion, such as the upper jaw portion 84. As the lower jaw closes and moves the lower jaw portion 82 toward the upper jaw portion 84, compressive forces are applied to the wires 94, 96, which cause the tongue portion 97 to bulge upwardly relative to the lower jaw portion 82.

As shown in FIG. 14, portions of the wires 94, 96 can be contained within coils 90, 91, 92, 93 to help support the portions of the wires that extend between the upper jaw portion 84 and the lower jaw portion 82 and the portions of the wires that pass through the lower jaw portion. The coils can comprise helically coiled metal wires, such as superelastic metal wires. In the illustrated embodiment, two of the four wires 94 are partially contained in the coil 90 and the other two of the wires 94 are partially contained in the coil 91. Similarly, two of the four wires 96 are partially contained in the coil 92 and the other two of the wires 96 are partially contained in the coil 93. The coils can help provide rigidity and column strength to prevent the wires from buckling in the region between the upper and lower jaw portions when the patient closes the patient's jaws. At the same time, the coils allow for flexion as they pass through a curved pathway through the lower jaw portion 82. The coils can also provide a spring biasing effect to help the wires return the un-articulated state when the patient opens the patient's jaws.

The prosthesis 80 can also comprise guide tubes 86, 87, 88, 89 that are secured to, or pass through, the lower jaw portion 82 on the left and right sides. The wires 94 and the coils 90, 91 are routed through the left guide tubes 86, 87, while the wires 96 and the coils 92, 93 are routed through the right guide tubes 88, 89, such that the guide tubes control the path of the wires and coils as the patient's jaws close. As shown, two wires within one coil pass through each individual guide tube, though in other embodiments, each wire can pass through its own guide tube within its own coil, and/or two or more coils can pass through the same guide tube. The guide tubes 86, 87, 88, 89 can comprise a low friction material, such as a polymeric or metallic material, that allows the coils to slide through the tubes with minimal friction. The guide tubes can be oriented in a curved path to cause the wires and coils to deform along the curved path as they are pushed through the guide tubes. When the patient's jaw closes, the upper jaw portion 84 pushes the wires 94, 96 and the coils 90,91, 92, 93 down through the guide tubes 86, 87, 88, 89 such that a larger portion of the wires become located in the tongue portion 97, causing the tongue portion to bulge upward relative to the lower jaw portion 82.

FIGS. 17-22 show another exemplary intra-oral prosthesis 100 that comprises a lower jaw portion, or anchor portion, 102 that couples the prosthesis to the lower dental arch or the adjacent area of the lower jaw. The lower jaw portion 102 can be secured to the lower jaw, such as with an adhesive or friction fit, and can be removable from the lower jaw to allow the patient to readily insert and remove the prosthesis 100 as needed.

Figure 17:
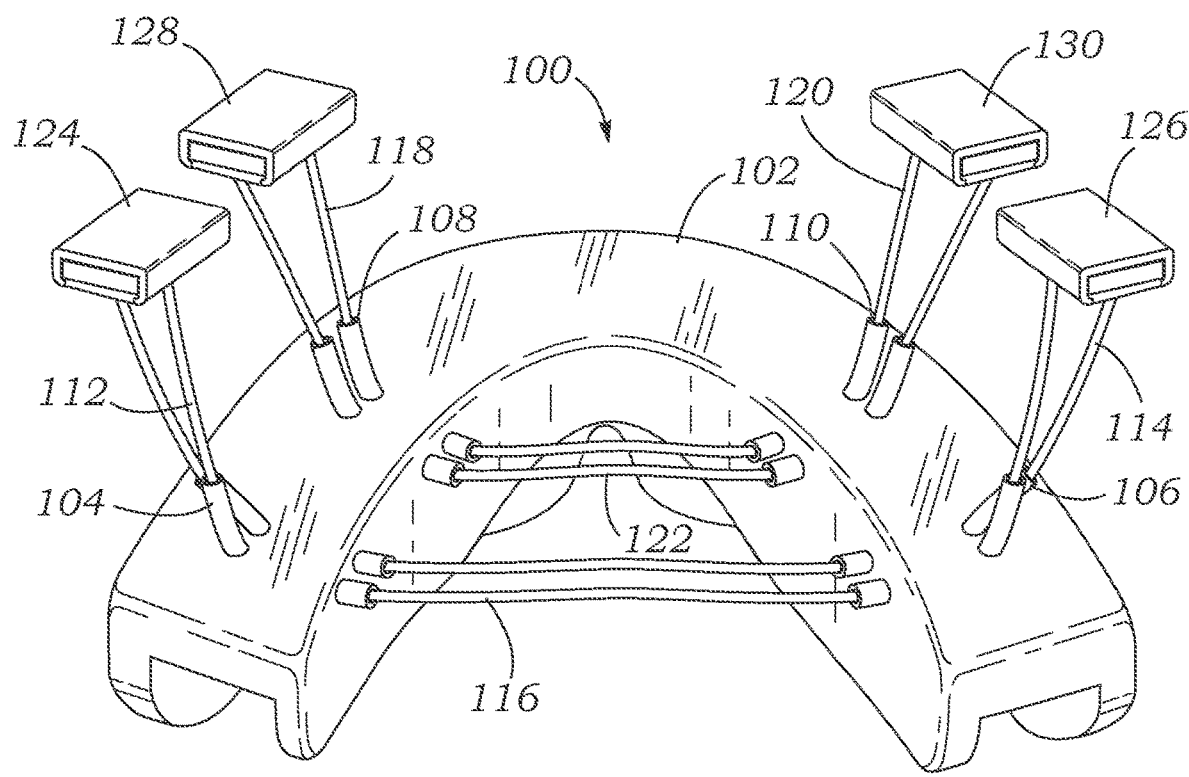
FIG. 17 is a posterior view of yet another intra-oral prosthesis.
Figure 22:
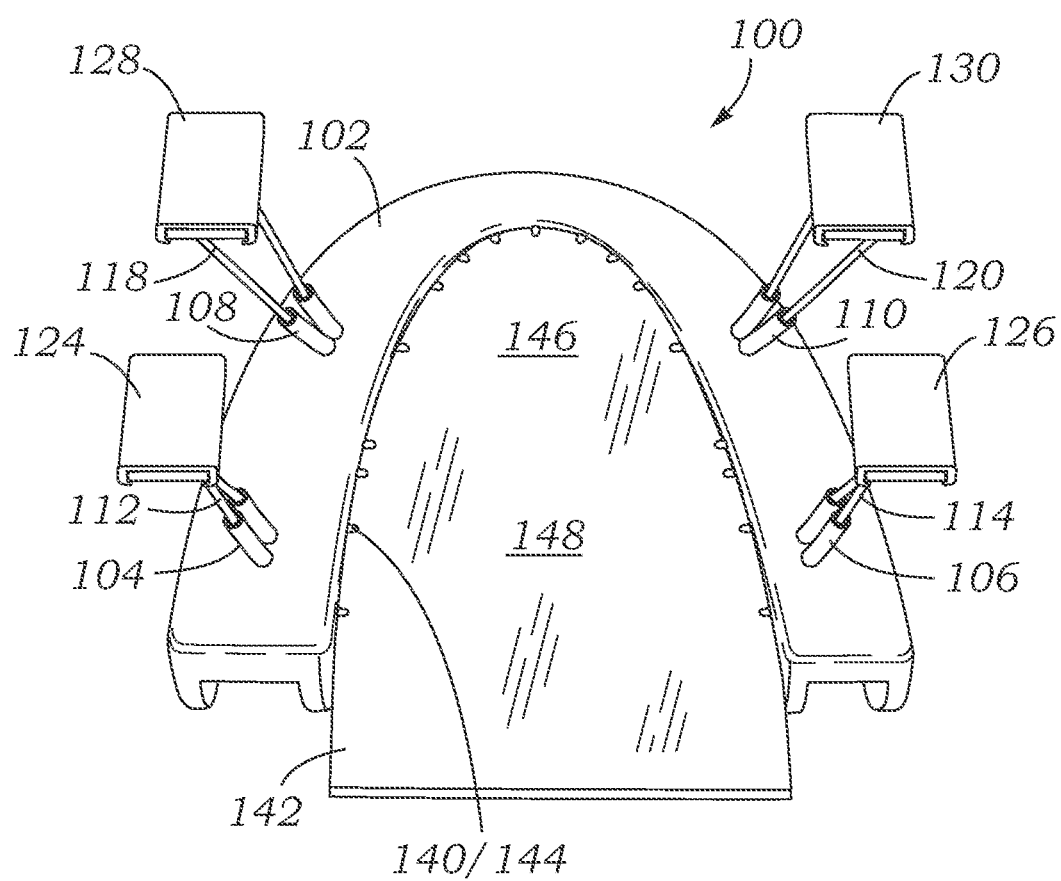
FIG. 22 shows tongue cover of FIG. 21 mounted on the intra-oral prosthesis of FIG. 20.

The prosthesis 100 further comprises a tongue portion having a posterior region 148 and an anterior region 146 (see FIG. 22). As shown in FIG. 17, the posterior region 148 is formed in the area of laterally extending flexible wires 116 and the anterior region 146 is formed in the area of the laterally extending flexible wires 122. The posterior and anterior regions of the tongue portion are each configured to independently, or with partial inter-dependence, bulge upwardly and/or posteriorly from the lower jaw portion 102, optionally in a predetermined sequence, when the patient's lower jaw closes upwardly toward the upper jaw, in order to simulate the native tongue motion during swallowing. In other embodiments, the tongue portion can bulge downwardly from an anchor portion anchored to the upper jaw, such that the tongue portion presses against or cooperates with the native tongue or a prosthetic tongue to help shape and propel a fool bolus posteriorly.

As shown in FIGS. 18-20, the tongue portion can also include additional flexible wires 132 that are oriented primarily in the anterior/posterior direction. The wires 132 can be thinner than the wires 116, 122, such as having a thickness or diameter of about 0.008 inches. The wires 132 can be woven with, welded to, or otherwise engaged with the laterally extending wires 116, 122 to form a lattice structure that provides a three-dimensional upward bulging in the anterior region and/or in the posterior region when the jaw is closed. The posterior ends of the wires 132 can be curved to meet at a common juncture 134 and/or the anterior ends of the wires 132 can be curved to meet at a common juncture 136. The juncture 134 and/or the juncture 136 can be bent downwardly relative to the intermediate portions of the wires 132 to conform to the native anatomy and/or to help direct food bolus for swallowing. The junctures 132, 134 can also allow the anterior and/or posterior ends of the tongue portion to be free from (not directly attached to) the lower jaw portion 102. Alternatively, the anterior ends of the wires 132 can be affixed to the lower jaw portion 102 at individual or common locations.

The wires 116, 122, and/or wires 132 can also be flattened, rectangular, ovular, tubular, or otherwise non-circular in cross-section, to adjust their resistance to bending and cause the wires to deform more readily in certain directions and deform less in other directions. For example, the wires 116, 122 can be flat strips that are thin (e.g., about 0.014 inches) in the superior-inferior direction and wider (e.g., about 0.030 inches) in the posterior-anterior direction, such that they naturally tend to bulge up in the superior direction and resist bending in anterior-posterior directions.

The wires 116, 122 and/or wires 132 can comprise a superelastic material, such as Nitinol or similar metal alloys, which allows the wires to be pre-formed in a desired shape and helps control the deformation properties of the wires during articulation of the jaw.

The tongue portion can be covered with a flexible layer of material, such a polymeric sheet 142 as shown in FIGS. 21 and 22, that provides a solid surface to the top of the tongue portion to better assist in moving a food bolus posteriorly. The sheet 142 can be removable and re-attachable to the lower jaw portion 102 or to the wires 116, 122, and/or 132 to allow the patient to replace the sheet 142 and/or clean the prosthesis 100. For example, the sheet 142 can comprise hooks/loops 144 (see FIG. 21) or other fasteners that engage with hooks/loops 140 or other fasteners around the inner perimeter of the lower jaw portion 102 (see FIG. 20). The flexibility of the sheet 142 can also facilitate independent bulging of the anterior region 146 and the posterior region 148 of the tongue portion, such as in a desired sequence to help with swallowing. The sheet 142 can optionally comprise ridges, grooves, or other contours to help shape the food bolus and/or help direct the bolus for swallowing.

The lateral wires 116, 122 can extend laterally across the tongue portion and through the left and right sides of the lower jaw portion 102 and terminate at actuation portions that contact a portion of the mouth opposite from the anchor portion, such as at the upper jaw. As illustrated, the left-upper ends 112 of the wires 116 are coupled to a left-posterior upper jaw contact 124, and the right-upper ends 114 of the wires 116 are coupled to a right-posterior upper jaw contact 126. Similarly, the left-upper ends 118 of the wires 122 are coupled to a left-anterior upper jaw contact 128, and the right-upper ends 120 of the wires 122 are coupled to a right-anterior upper jaw contact 130. The upper jaw contacts 124, 126, 128, 130 engage with the patient's upper jaw, such as with the upper teeth, gums, and/or with tissue of the palate. The upper jaw contacts can comprise individual pads configured to engage with different locations of the upper jaw. As the patient's lower jaw closes and moves the lower jaw portion 102 toward the upper jaw contacts 124, 126, 128, 130, compressive forces are applied to the wires 116, 122, which cause the anterior and posterior tongue portions 146, 148 to bulge upwardly relative to the lower jaw portion 102.

As shown in FIG. 17, the prosthesis 100 can also comprise guide tubes 104, 108, 106, 110 that are secured to, or pass through, the lower jaw portion 102 below the upper jaw contacts 124, 126, 128, 130. The wires 116, 122 are routed through the guide tubes such that the guide tubes can control the path of the wires as the jaw closes. In the example shown, the two posterior wires 116 pass through the two left-posterior guide tubes 104 and through the two right-posterior guide tubes 106, and the two anterior wires 122 pass through the two left-anterior guide tubes 108 and through the two right-anterior guide tubes 110. As shown, each guide tube is associated with one wire, though in other embodiments, two or more wires can pass through some or all of the guide tubes. The guide tubes can comprise a low friction material, such as a polymeric or metallic material, that allows the wires to slide through the tubes with minimal friction. The guide tubes can be oriented in a curved path to cause the wires to deform along the curved path as the wires are pushed through the tubes. When the patient's jaw closes, the upper jaw contacts 124, 126, 128, 130 push the upper ends 112, 114, 118, 120 of the wires 116, 122 down through the guide tubes 104, 108, 106, 110 such that a larger portion of the wires become located in the anterior and posterior regions 146, 148 of the tongue portion, causing the tongue portion to bulge upward relative to the lower jaw portion 102.

FIGS. 23-26 illustrate another exemplary intra-oral prosthesis 200 in various stages of assembly. The prosthesis 200 includes an arcuate lower jaw portion 202 that is configured to be coupled to a patient's lower dental arch to anchor the prosthesis inside the mouth. The prosthesis 200 also includes three independent groups of laterally extending flexible wires, including a posterior group 204, a middle group 206, and an anterior group 208 (FIG. 23). In alternative embodiments, the device can include any number of laterally extending wires per group and the device can include any number of groups (e.g. 1, 2, 4, or more) of laterally extending wires that act as independent modules to lift the tongue portion. The posterior group of wires 204 extend on each side through angled guide tubes 212 and form arches 210 at their ends above the lower jaw portion 202. The ends of the wires extend down from the top of the arches 210 and are fixed or coupled to the lower jaw portion 202. Similarly, the middle group of wires 206 extend on each side through angled guide tubes 216 and form arches 214 at their lateral ends, and the anterior group of wires 208 extend on each side through angled guide tubes 220 and form arches 218 at their lateral ends.

As shown in FIG. 24, the device 200 also includes upper jaw contact pads 224, 226, and 228 positioned over the wire arches 210, 214, and 216, respectively, on each side of the device. The contact pads can comprise a resiliently deformable material, such as silicone or other polymeric material, that provides a safe contact surface for the patient's upper dental arch to push against. The contact pads 224, 226, 228 can be attached to the lower jaw portion 202 on the lateral and medial sides of the respective arches to hold the contact pads in place over the wire arches. For example, the lateral ends of the contact pads can be secured to lateral surfaces of the lower jaw portion and the medial ends of the contact pads can be secured to medial surfaces of the lower jaw portion and/or to the cover layer 232 (FIG. 26). The contact pads can be removable and replaceable for purposes of cleaning them, replacing them when they are worn out, to access and clean the wire arches, and/or for other purposes.

As shown in FIG. 24, the laterally extending wire groups 204, 206, 208 can optionally be coupled together with one or more anterior-posterior extending wires 222, which can be welded, adhered, wound, woven, or otherwise coupled to the laterally extending wires 204, 206, 208 to form a grid or lattice or mesh in the tongue portion. In some embodiments, the wires can be coupled together using laser welding techniques. This can provide a more continuous support and force distribution across the bulging tongue portion.

As shown in FIG. 25, the tongue portion can include a thick mass 230 that can comprise silicone or other polymeric material and overlies the wires 204, 206, 208, 222. The mass 230 can be shaped in the general shape of a native tongue in order to allow the device 200 to more closely simulate the functions of a native tongue. The mass 230 can also help elevate the cover layer 232 higher in the mouth when the jaws close to better simulate the full motion and function of a native tongue. The mass 230 can be flexible enough to allow the three wire groups 204, 206, 208 to independently bulge upward without the mass separating from the wires. The mass 230 can also provide a solid, continuous surface underneath the cover layer to assist with swallowing and other oral functions.

As shown in FIG. 26, the cover layer 232 overlies the mass 230 and can be secured around its lateral and anterior perimeter to the lower jaw portion 202, such as with attachments 234, which can comprise any type of attachment or fasteners, such as hooks, loops, staples, clips, tethers, rivets, pins, etc. The posterior edge of the cover layer 232 can also be secured to the wires 204, wires 222, and/or to the mass 230. The cover layer 232 can comprise latex, nitrile, or other flexible polymeric materials, for example. The cover layer 232, mass 230, and/or the contact pads 224, 226, 228 can be disposable and replaced periodically, or can be cleanable and reusable.

In use, the lower jaw portion 202 is placed over the patient's lower dental arch to secure the device in the mouth with the contact pads 224, 226, 228 below the upper dental arch. When the user closes his jaws, the upper dental arch contacts the contact pads 224, 226, 228, which transmit force down to the wire arches 210, 214, 218, causing the medial aspect of the wire arches to slide down through the guide tubes 212, 216, 220 while the lateral aspect of the wire arches remains fixed to the lower jaw portion 202. As the laterally extending portions of the wires in groups 204, 206, 208 are compressed, they bulge upwardly, lifting the mass 230 and the cover layer 232 to simulate the function of a native tongue. When the user open his jaws, the wires resiliently return back to the configuration shown in FIG. 23, and the tongue portion moves back down to the configuration shown in FIG. 26.

FIGS. 27 and 28 show another exemplary intra-oral prosthetic device 300 that is similar in configuration and function to the device 200, though it includes an acrylic (or similar material) lower jaw portion 302 that is custom shaped to fit a particular patient's lower dental arch. The device 300 includes the lower jaw portion 302, an anterior laterally extending wire 304, a middle laterally extending wire 306, and a posterior laterally extending wire 308, which are coupled via anterior-posterior extending wires 322. The laterally extending wires pass through tubes 312, 316, and 320 that are coupled to or form in the lower jaw portion 302. The lateral ends of the wires form arches 310, 314, and 318 similar to those in the device 200. The arches can also be covered with contact pads (not shown) is a matter similar to the device 200. A cover layer 330 is shown overlaying the wires in the tongue portion.

As shown in FIG. 28, the underside of the lower jaw portion 302 can be formed to fit the anatomy of the user lower dental arch. In FIG. 28, indentations 340 are shown in the lower surface of the lower jaw portion 302, which can be formed, for example, by pressing the lower jaw portion 302 against the user's lower dental arch while it is in a malleable state and letting it solidify in that shape. This feature can be included in any of the disclosed intra-oral prosthetic devices and can help the device 300 better anchor to the user's lower jaw when in use.

Table 1 below lists experimental data regarding pressures and forces that the tongue portion of an exemplary intra-oral prosthesis as disclosed herein can apply against a patient's hard palate when the patient closes the patient's jaws.

TABLE 1

Pressure exerted on the hard palate by exemplary prosthetic tongue

| | Number | | | | | |
|---|---|---|---|---|---|---|
| | 1 | 2 | 3 | 4 | 5 | Ave. |
| Weight (kg) | 0.0174 | 0.017 | 0.0202 | 0.0192 | 0.0183 | 0.01842 |
| Force (N) | 0.170 | 0.167 | 0.196 | 0.188 | 0.180 | 0.180 |
| Pressure (kPa) | 27.20 | 26.72 | 31.36 | 30.08 | 28.80 | 28.80 |

By comparison, an exemplary range pressures provided by the native tongue in healthy humans are as follows: 41.8±13.6 kPa (anterior), 31.8±14.5 kPa (middle), and 29.8±14.9 kPa (posterior). The experimental data in Table 1 approaches these physiologic goal tongue pressures.

In other experimental tests, measured average pressures exerted between the bulging tongue portion against the hard palate are as follows: 22.2±1.3 kPa (anterior) and 22.4±1.34 kPa (posterior). These measurements were taken using an IOPI pressure sensing device. In other experimental tests using a MOST pressure sensing device, measured average pressures exerted between the bulging tongue portion against the hard palate are as follows: 34.7±8.92 kPa (anterior) and 27.32±2.19 kPa (posterior). Pressures applied by intra-oral prostheses can be customized to match physiologic tongue pressures, such as by modifying the wire number, diameter, and geometry (e.g., round wires, rectangular strips, or tubes) and/or by adding different types of covers over the tongue portion.

FIGS. 29A-29D illustrate exemplary testing parameters that were used for testing the amount of resistance force caused by the guide tubes that must be overcome when using various versions of the device 100 shown in FIG. 29A (and FIG. 17) in order to press down the contact pads 124-130 and cause the wires 116 and 122 to bulge up. Testing was conducted uses several different tube embodiments representing the guide tubes 104-110 of the device 100.

FIG. 29B shows the tested values for the parameters of tube diameter, tube length, and tube bend angle. FIG. 29C shows nine different sized guide tubes having three different lengths (7 mm, 9 mm, 11 mm) and three different diameters (4 Fr, 5 Fr, 6 Fr). FIG. 29D shows three different tube bend angles tested (90°, 120°, 150°). Various different tube configurations resulted in significantly different resistance force results.

Figure 30:
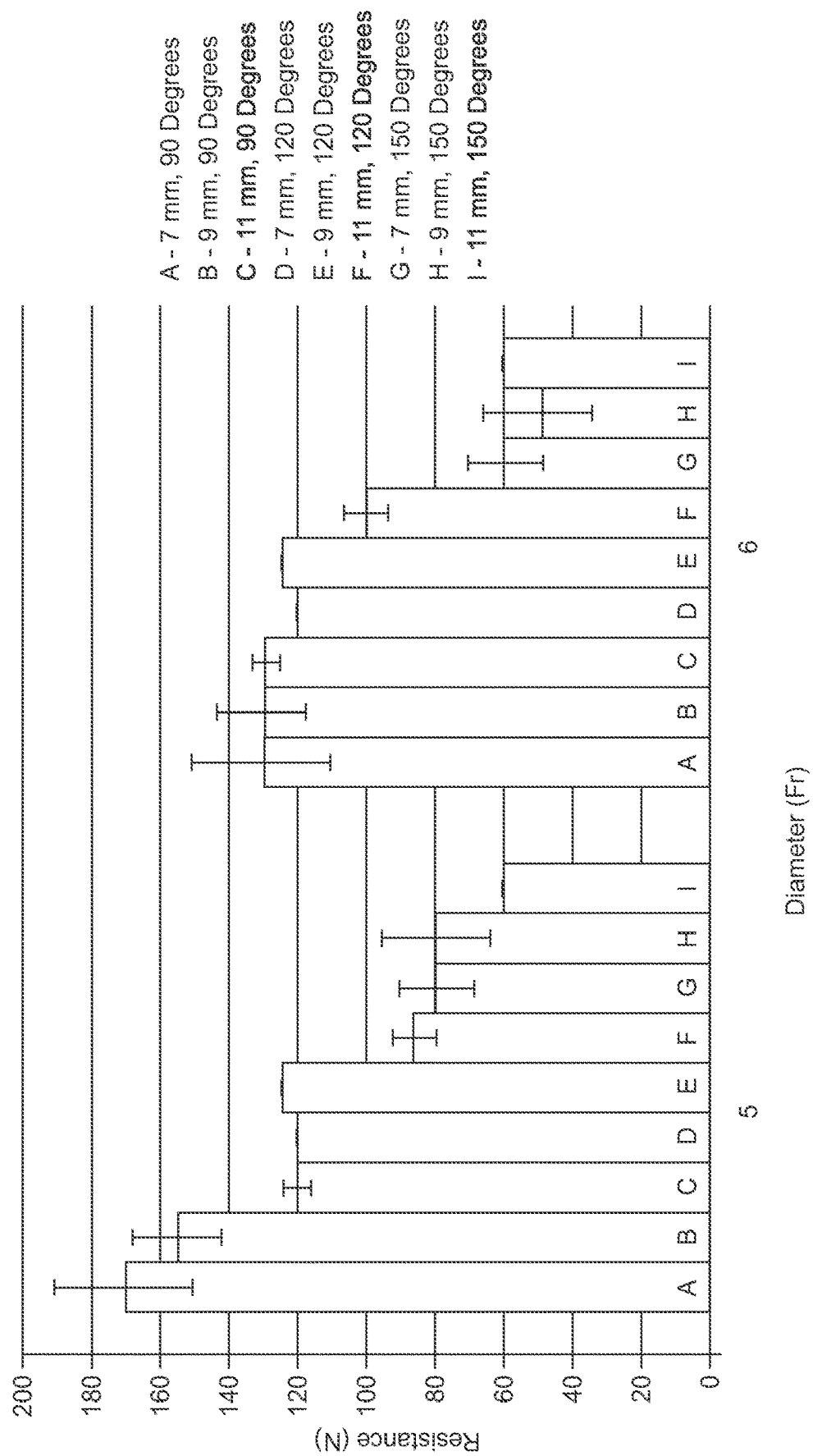
FIGS. 30-32 are graphs showing test results for resistance created by tubes of various diameters, lengths, and angles.

FIG. 30 shows test results for measured resistance (Newtons) for a first group of tubes with a 5 Fr diameter (left group) and second group of tubes with a 6 Fr diameter (right group). In each group, different combinations of length and bend angle were tested. As can be seen in FIG. 30, tubes with the larger diameter (6 Fr) provides only slightly less resistance in general compared to the smaller diameter tubes (5 Fr), though the differences were not very significant.

Figure 31:
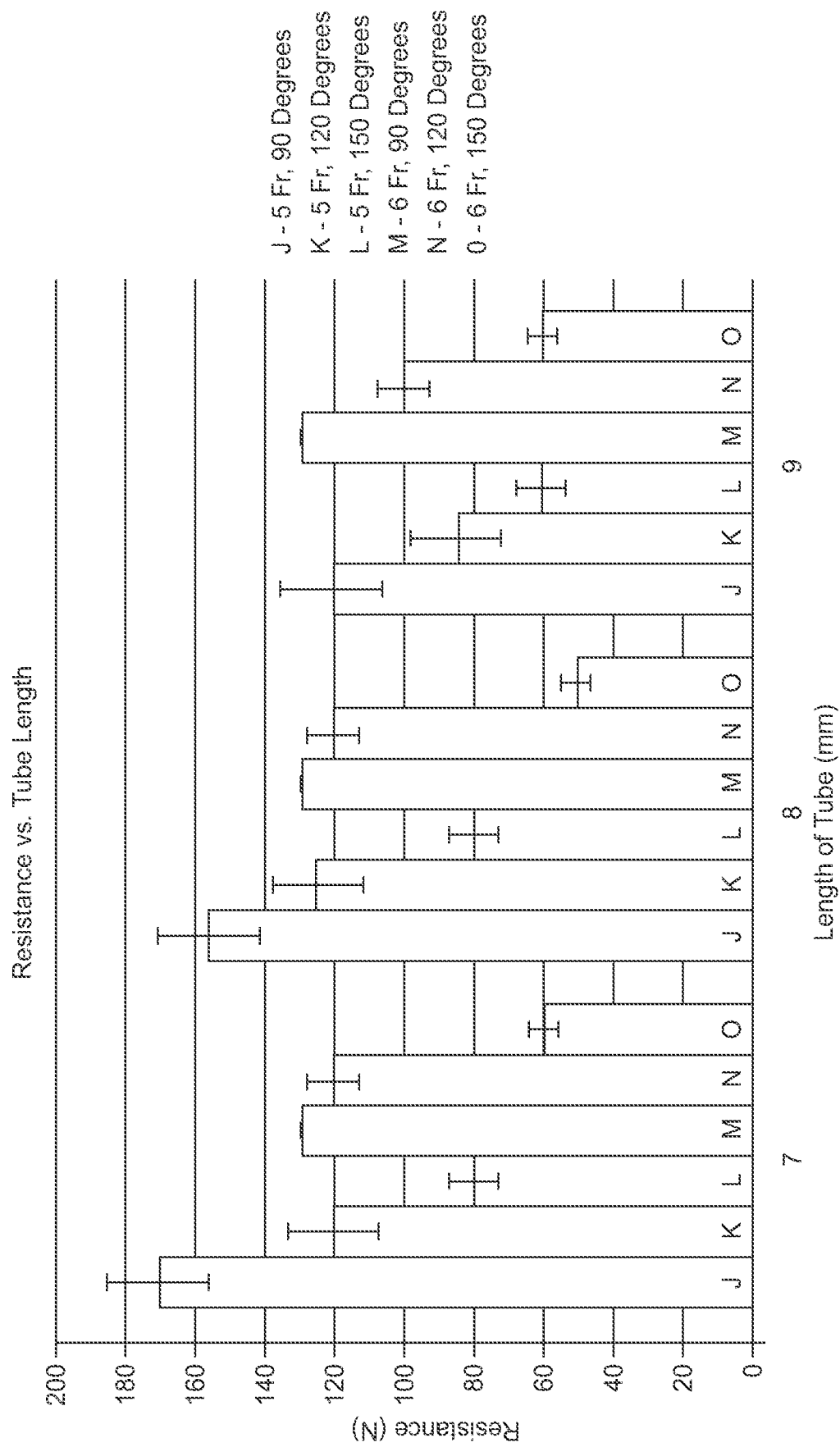

FIG. 31 shows test results for measured resistance (Newtons) sorted by length, with a first group of tubes with a 7 mm length (left group), a second group of tubes with an 8 mm length (middle group), and third group of tubes having a 9 mm length (right group). Each group includes different combinations of diameter and bend angle. As can be seen in FIG. 31, the differences in length resulted in no significant differences in resistance for the larger 6 Fr tubes, but showed more resistance at shorter lengths for the 5 Fr tubes, particularly for the 5 Fr, 90° tubes.

Figure 32:
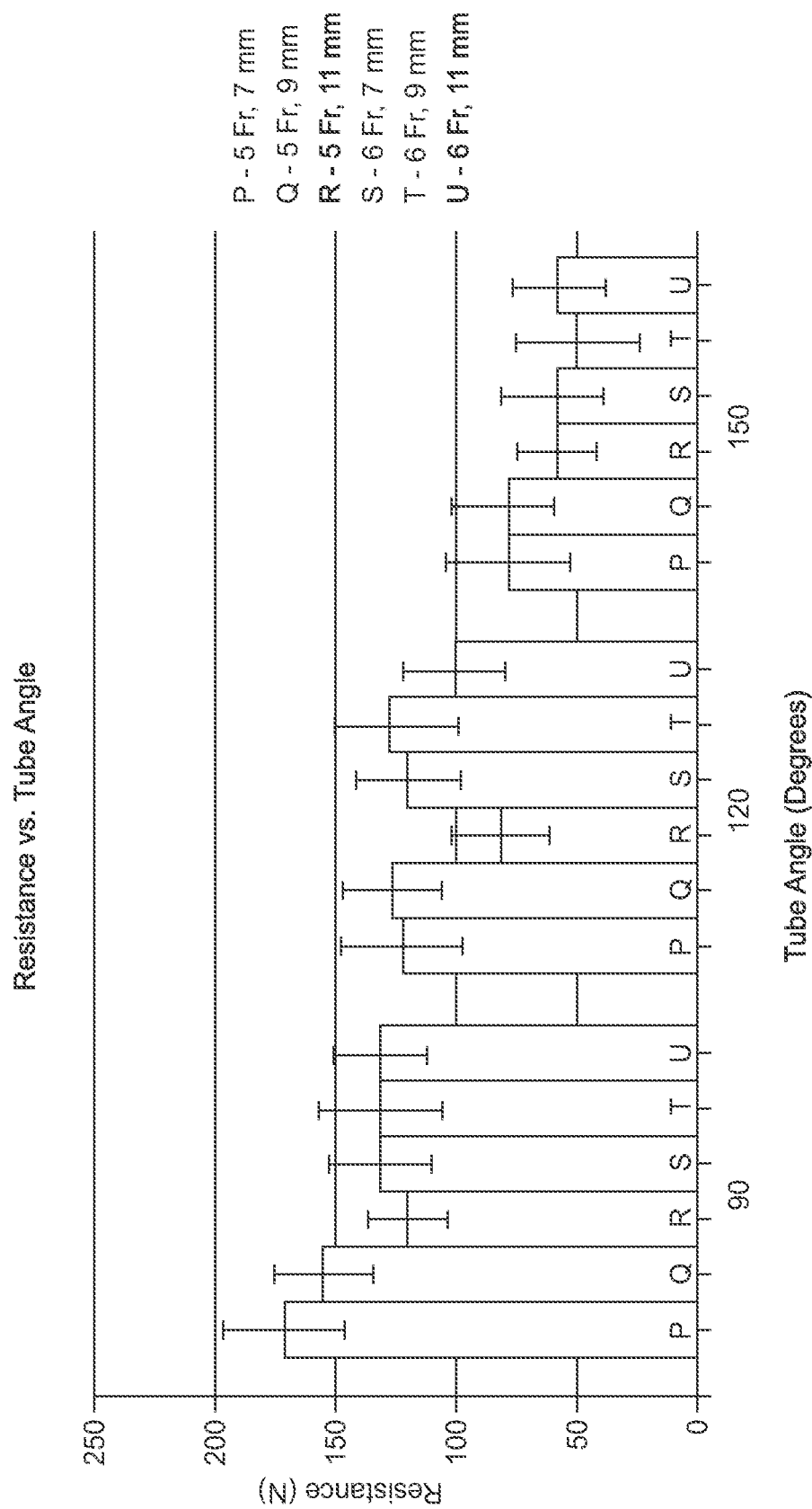

FIG. 32 shows test results for measured resistance (Newtons) sorted by bend angle, with a first group of tubes with a 90° bend angle (left group), second group of tubes with a 120° bend angle (middle group), and third group of tubes having a 150° bend angle (right group). Each group includes different combinations of diameter and length. As can be seen in FIG. 32, the greater bending angles showed the least resistance. The range of resistance forces for the tubes with 90° bend angle is 100 N to 200 N, which may be practical for a prosthetic tongue device. The resistance forces observed for the 150° bend angle are in the range of 40 N-100 N (p-value<0.01), which demonstrates a significant reduction of the resistance during the wire motion through the tubes. While the resistance with 150° bent tubes is least, and can be preferable in certain embodiments, a lower bend angle may cause other undesired effects in certain embodiments. For example, a lower angle can reduce the ability of the wires to spring back and recover their shape in certain embodiments. Therefore, guide tubes having a 120° bend angle may be used in some embodiments to provide a compromise between sufficiently low resistance forces and sufficient ability of the wires to spring back and recover their shape.

FIGS. 33-36 illustrate measured pressure values applied by the tongue portions of various intra-oral prosthetic device embodiments. Two pressure measurement systems, the IOPI (Iowa Oral Performance instrument) (IOPI® Model 2.3, WA) and MOST (Madison Oral Strengthening Therapeutic device, Swallowsolutions Model 1.5 WI) were used to measure the upward pressure produced by the prosthetic tongue portions when the devices were actuated. Both of these devices are commonly used in exercise therapy to assist patients with oral motor problems such as dysphagia. The masticatory action is complicated and the exerted force during it is not constant; measuring bite force is introduced as an indicator of the masticatory system and can be dependent on the gender, age, craniofacial morphology, type of the food, and the measurement techniques. In general, it is desirable that practical prosthetic embodiments should produce sufficient pressure required to push food during the swallowing process for a particular patient's anatomical parameters. The sensors of the MOST system are smaller and more sensitive compared with the sensor in the IOPI device and can record the maximum pressure with higher precision, especially when the pressure is locally concentrated on a small area.

Figure 33:
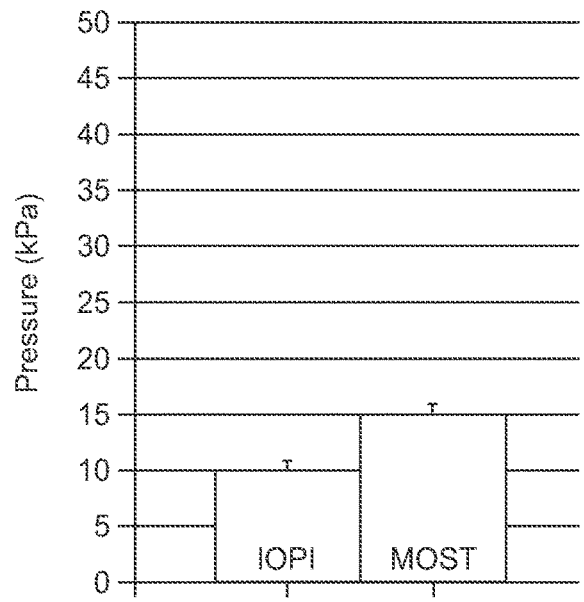
FIG. 33 shows the upward pressure produced by the tongue portion 48 of the device 40 shown in FIGS. 6-9 when the upper jaw contacts 54, 56 are depressed, as measured using two different force measurement devices.
Figure 34:
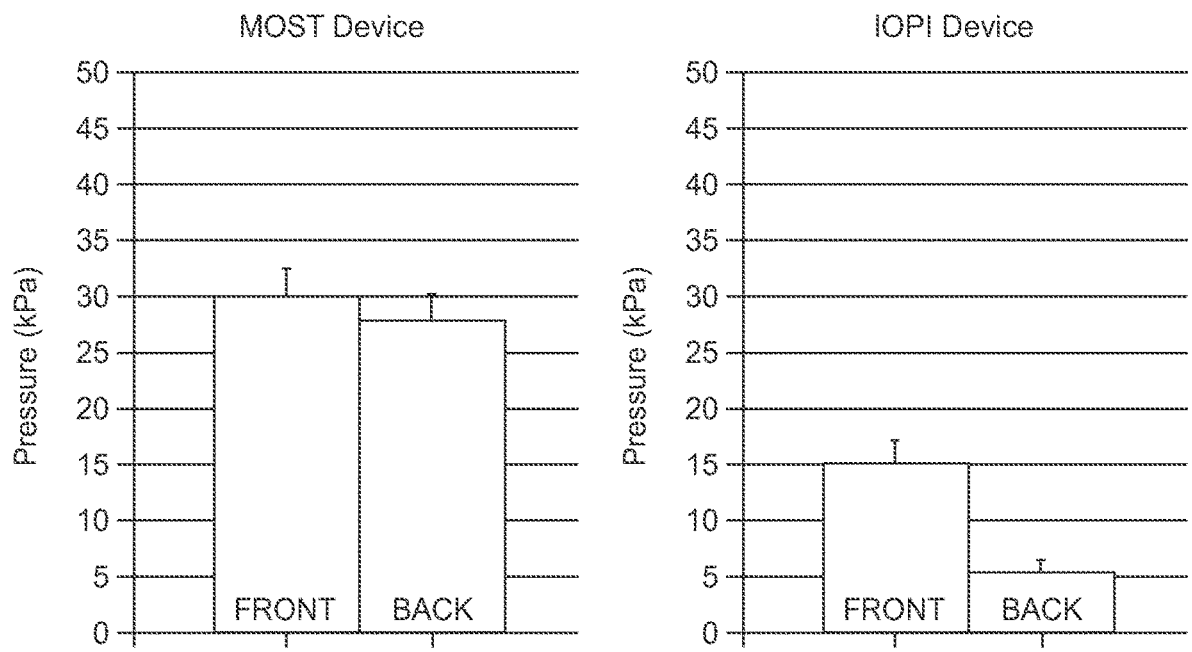
FIG. 34 shows the upward pressure produced by the rear wires 116 and the front wires 122 of the device 100 shown in FIG. 17 (without the connecting lattice wires 132 shown in FIGS. 18-20) when the upper jaw contacts 124-130 are depressed, as measured using two different force measurement devices.
Figure 35:
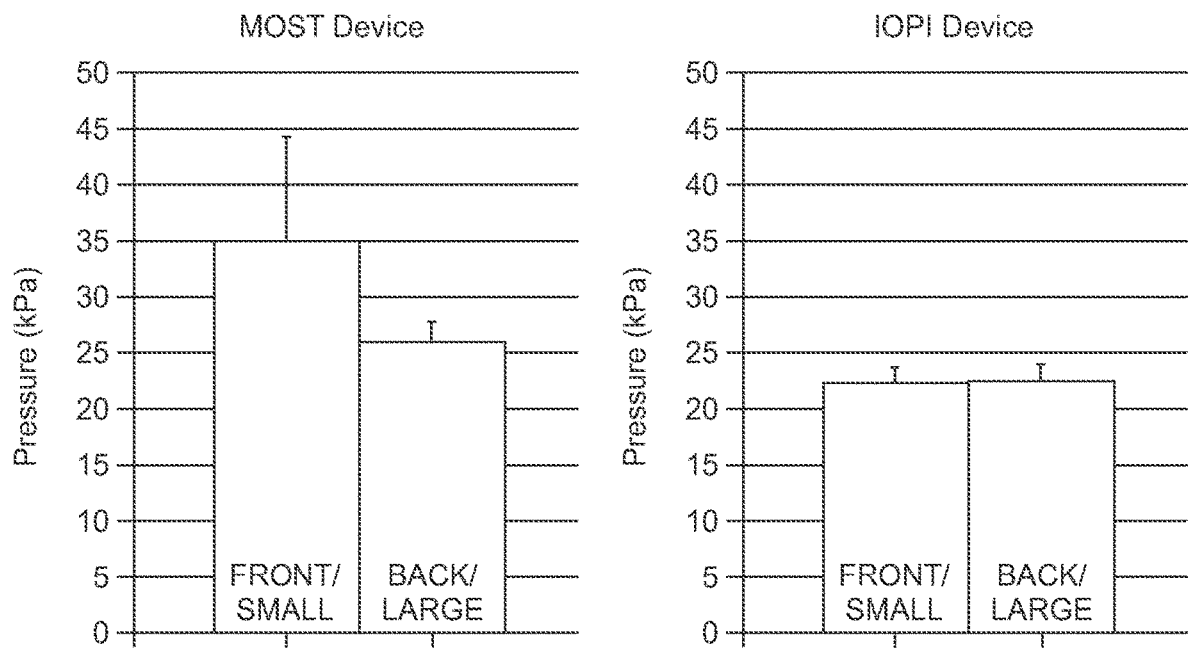
FIG. 35 shows the upward pressure produced by the rear wires 116 and the front wires 122 of the device 100 shown in FIGS. 18-20 (including the connecting lattice wires 132) when the upper jaw contacts 124-130 are depressed, as measured using two different force measurement devices.
Figure 36:
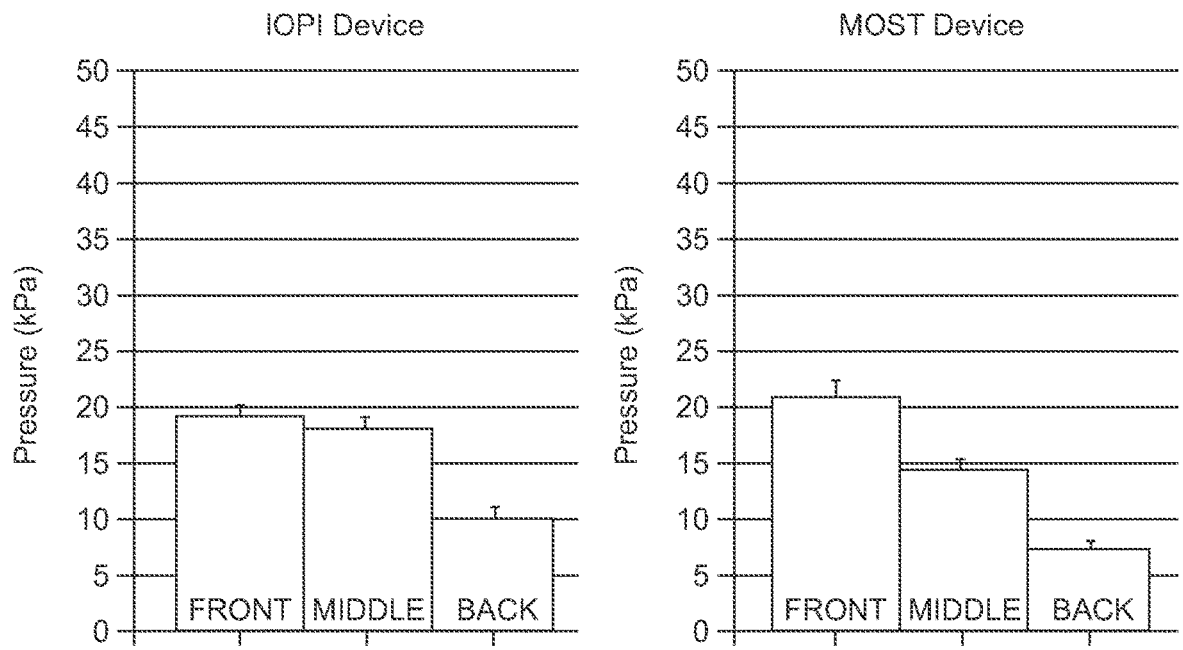
FIG. 36 shows the upward pressure produced by the rear wires 204, middle wires 206, and front wires 208 of the device 200 shown in FIGS. 23-26 (including the connecting lattice wires 222, semi-rigid covering 230, and cover layer 232) when the upper jaw contacts 224-228 are depressed, as measured using two different force measurement devices.

FIG. 33 shows the upward pressure produced by the tongue portion 48 of the device 40 shown in FIGS. 6-9 when the upper jaw contacts 54, 56 are depressed, as measured using the IOPE and MOST devices. FIG. 34 shows the upward pressure produced by the rear wires 116 (BACK) and the front wires 122 (FRONT) of the device 100 shown in FIG. 17 (without the connecting lattice wires 132 shown in FIGS. 18-20) when the upper jaw contacts 124-130 are depressed, as measured using the MOST device (left graph) and the IOPI device (right graph). FIG. 35 shows the upward pressure produced by the rear wires 116 (BACK/LARGE) and the front wires 122 (FRONT/SMALL) of the device 100 shown in FIGS. 18-20 (including the connecting lattice wires 132) when the upper jaw contacts 124-130 are depressed, as measured using the MOST device (left graph) and the IOPI device (right graph). FIG. 36 shows the upward pressure produced by the rear wires 204 (BACK), middle wires 206 (MIDDLE), and front wires 208 (FRONT) of the device 200 shown in FIGS. 23-26 (including the connecting lattice wires 222, semi-rigid covering 230, and cover layer 232) when the upper jaw contacts 224-228 are depressed, as measured using the IOPI device (left graph) and the MOST device (right graph).

As can be seen in FIGS. 33-36, the range of applied pressures measured from all the tested embodiment was roughly in the range of from 5 kPa to 35 kPa. According to both MOST and IOPI devices, the greatest pressure was observed using the embodiment 100 of FIGS. 18-20 (FIG. 35) and the lowest pressure was observed using the embodiment 40 in FIGS. 6-9 (FIG. 33). In each of the tested embodiments having distinct front and rear portions, the recorded pressure in the front position is higher than the rear position.

The normal tongue pressures exerted from normal adults are approximately 56 kPa. The embodiment 100 of FIGS. 18-20 (FIG. 35) shows the closest pressure to that of the normal adult levels, showing roughly 35 kPa. The crossing latticework shape of this design is a significant reason that it provides higher pressure relative to the other tested embodiment.

Furthermore, the maximum mouth opening height dimension for a patient can be in the range of 32 mm to 77 mm. Therefore, the raising height of the tongue portion in a practical embodiment can desirably be sufficient to allow the tongue portion to reach the roof of the mouth for patients having this range of maximum mouth opening height. Also, the overall size the device should be small enough to fit into the patient's mouth and remove from the patient's mouth during normal use for this range of mouth sizes. The embodiments 200 and 300 illustrated in FIGS. 23-28 can provide a low profile size for inserting and removing the device from the mouth, and at the same time can provide sufficient raising height of the tongue portions, which can be augmented by including the mass 230 (FIG. 25) or similar component, under the cover layer 232.

In any of the disclosed embodiments, the wires in the tongue portion of the device can include thickened regions, beads, balls, welds, kinks, cross-bars, or similar structures (referred to collectively as "stops"), that limit the degree to which the wires can pass through the guide tubes. Such stops can be located on the laterally extending wires medial to the guide tubes. When the patient opens his jaws and the bulged-up tongue portion resiliently moves back down, the stops can limit how far down the bulge recoils and how far up the lateral ends/arches of the wire travel. This can help maintain a small degree of bulge in the tongue portion in the relaxed state so that the wires are biased to bulge in the proper direction. The stops can also help ensure a desired height of the contact pads on either side below the upper teeth, and help ensure a desired resting height of the tongue portion so that the tongue portion can reach the desired height when the user closes his jaws.

Figure 37:
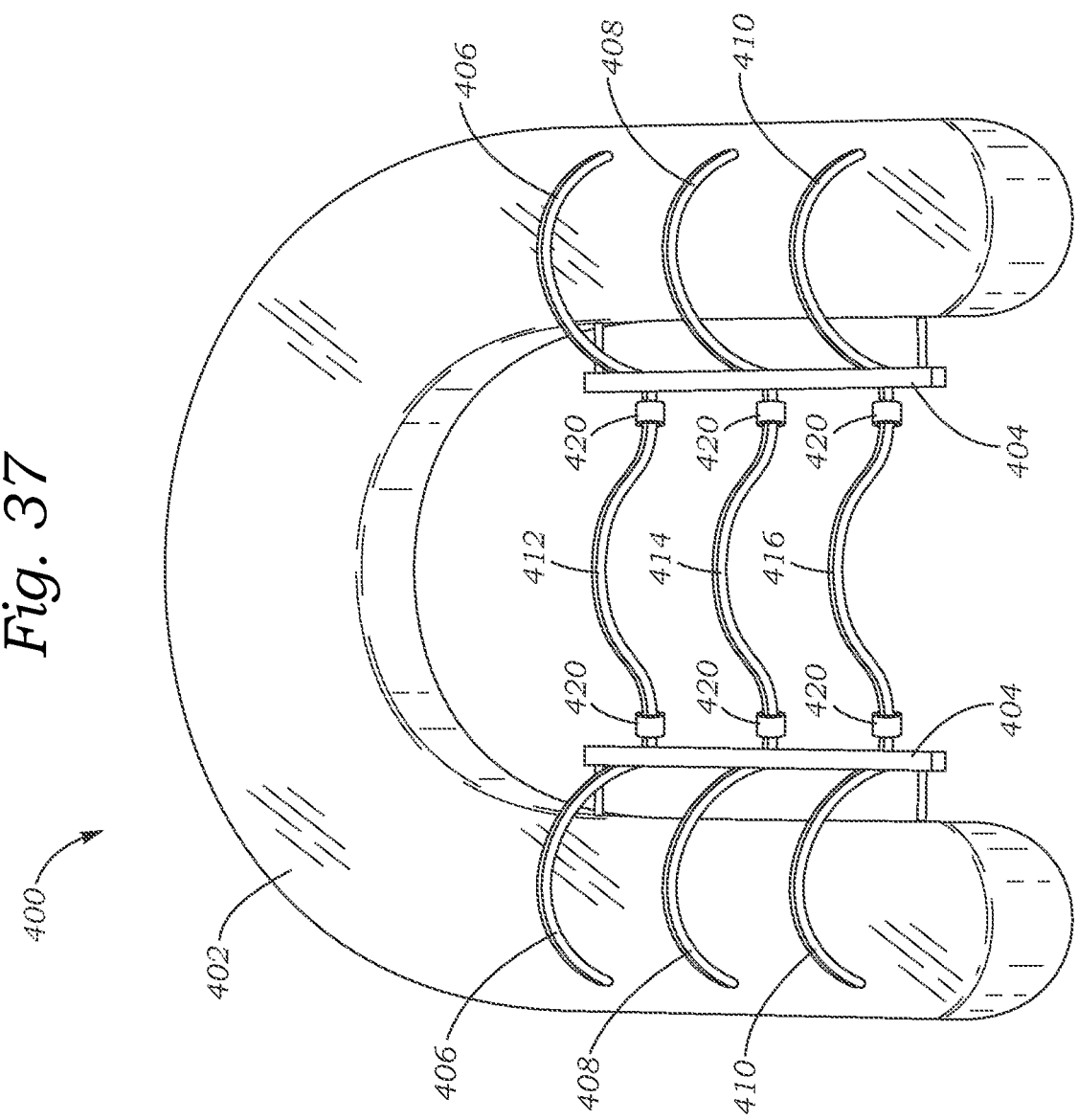
FIG. 37 shows another exemplary prosthetic device that includes rigid guide bars instead of guide tubes, and the resilient wires pass under the guide bars. The wires also include stops medial to the guide bars to limit the motion of the wires relative to the bars.

FIG. 37 shows another exemplary prosthetic device 400 that includes guide bars instead of guide tubes to control the motion of the wires. The device 400 includes a body 402 that can couple the device to the lower dental arch to anchor it in the mouth, three resiliently flexible wires 406, 408, 410 that extend across between the left and right sides of the body 402, two guide bars 404 fixed to the left and right sides of the body, and stops 420 mounted on the wires to limit their motion relative to the guide bars.

Each of the flexible wires (there can be any number though three are shown in this example) can be attached at its lateral ends to the body 402 and include arches above the left and right sides of the body to provide an actuation location. The wires 406, 408, 410 extend down from the arches and pass between the medial sides of the body 402 and the lateral sides of the bars 404, then curve underneath the bars 404 to the bulging portions 412, 414, 416 between the bars. The bars 404 can replace the functionality of the guide tubes described herein to help guide the direction of the wires from the arches toward the central bulging portions when the user closes his jaw. The bars 404 can be fixed directly to the body 402 our coupled to the body via an intermediate mounting member. The bars 404 can have any cross-sectional shape. Two or more bars can be present on either side instead of a single bar as shown. In an alternative embodiment, the bars 404 can include holes or notches in them through which the wires pass to further restrict and guide the motion of the wires.

The stops 420 can be included on the wires or as part of the wires (e.g., a thickened portion) just medial to the bars 404. The stops 420 limit the motion of the wires laterally under and past the bars. When the user opens his jaws and releases pressure from the arched portions of the wires, the central bulged portion resiliently moves back downward until the stops 420 contact the bars 404 on either side, at which point the central bulged portion can no longer move down any further and the motion stops. This helps maintain a small degree of bulge in the central bulged portion in the relaxed state so that the wires are biased to bulge in the proper upward direction then next time the user bites down. The stops 420 also help ensure a desired resting height of the tongue portion (not shown) that overlies the central bulged portion of the wires so that the tongue portion can reach the desired height when the user closes his jaws again.

Figure 38:
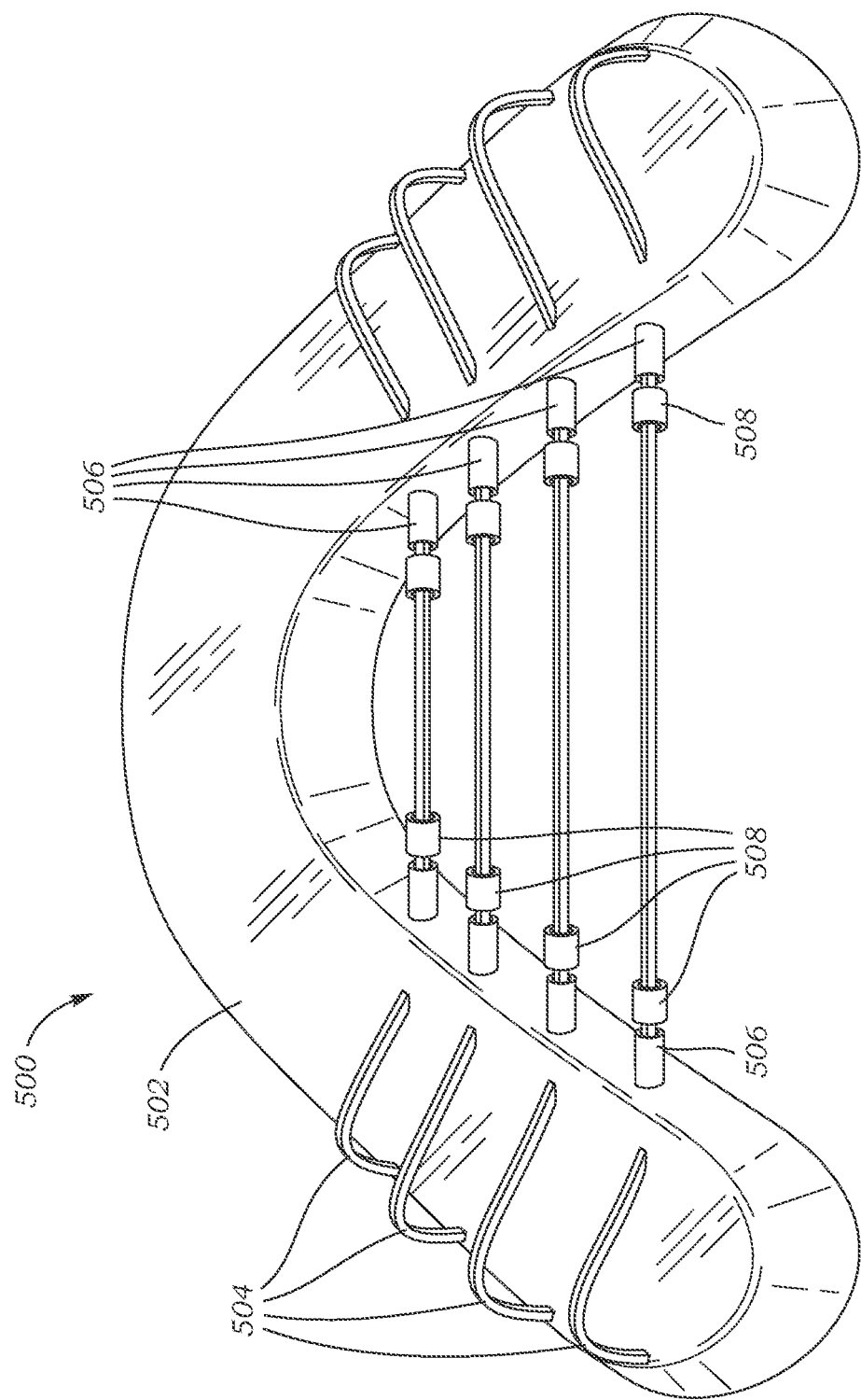
FIG. 38 shows another exemplary prosthetic device that includes four wires that pass through guide tubes and include stops positioned on the wires medial to the guide tubes to limit the motion of the wires relative to the guide tubes.

FIG. 38 shows another exemplary prosthetic device 500 that includes stops along with guide tubes instead of guide bars. Device 500 includes a body 502 that can couple the device to the lower dental arch to anchor it in the mouth, four resiliently flexible wires 504 that extend across between the left and right sides of the body 502, angled guide tubes 506 passing through the left and right sides of the body for each of the four wires 504, and stops 508 mounted on the wires to limit their motion relative to the guide tubes.

Each of the flexible wires 504 (there can be any number though four are shown in this example) can be attached at its lateral ends to the body 502 and include arches above the left and right sides of the body to provide an actuation location. The wires 504 extend down from the arches and the guide tubes 506 to a central bulging portion between the guide tubes. The guide tubes 506 can be similar is form and function to other guide tubes described herein.

The stops 508 can be included on the wires 504 or as part of the wires (e.g., a thickened portion) just medial to the guide tubes 506. The stops 508 limit the motion of the wires laterally through the guide tubes 506. When the user opens his jaws and releases pressure from the arched portions of the wires, the central bulged portion resiliently moves back downward until the stops 508 contact the medial ends of the guide tubes 506 on either side, at which point the central bulged portion can no longer move down any further and the motion stops. This helps maintain a small degree of bulge in the central bulged portion in the relaxed state so that the wires are biased to bulge in the proper upward direction then next time the user bites down. The stops 508 also help ensure a desired resting height of the tongue portion (not shown) that overlies the central bulged portion of the wires so that the tongue portion can reach the desired height when the user closes his jaws again.

Figure 39:
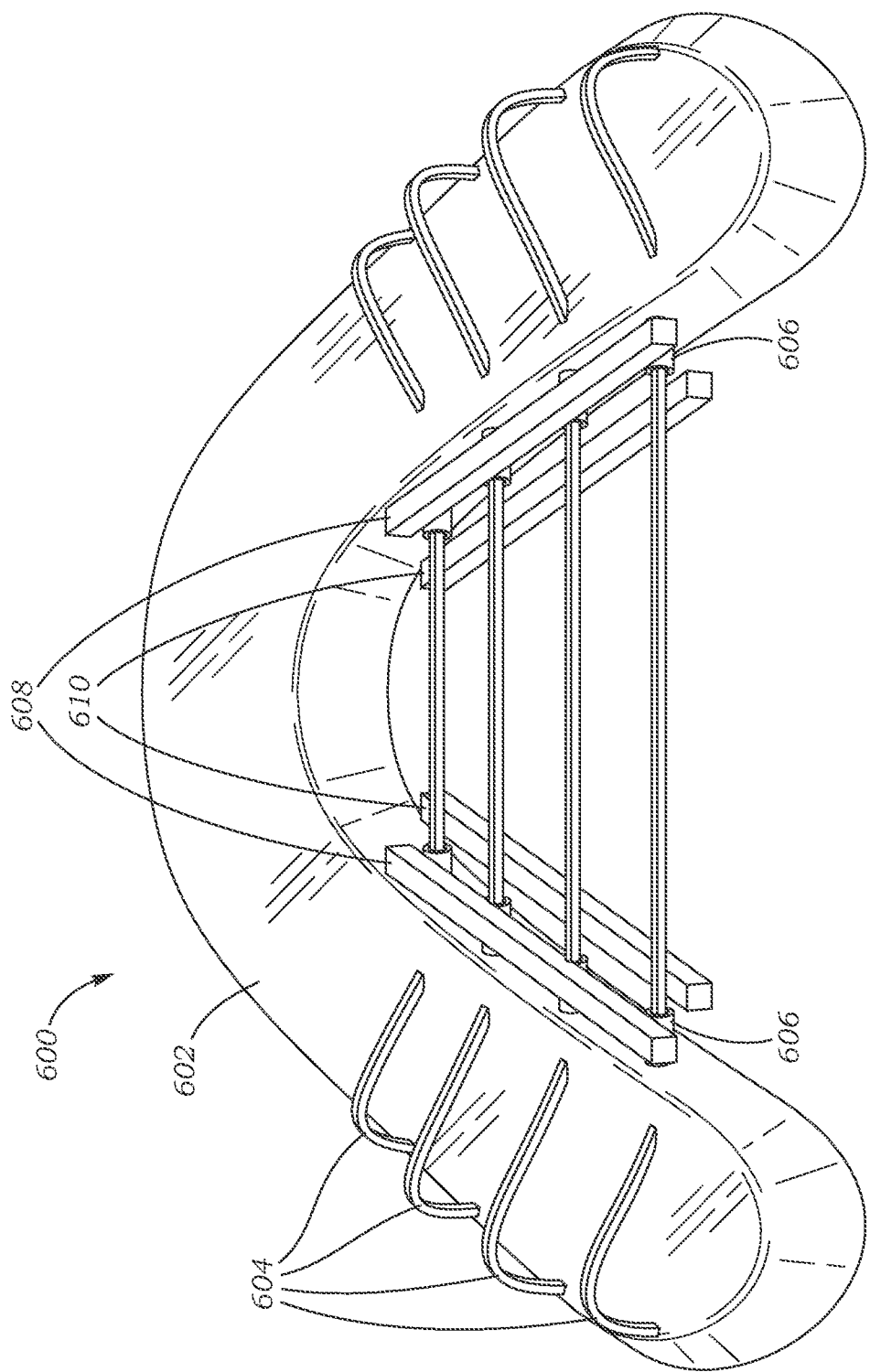
FIG. 39 shows another exemplary prosthetic device that includes guide tubes and guide bars. The resiliently flexible wires pass through the guide tubes and pass between upper guide bars and lower guide bars at either side.

FIG. 39 shows another exemplary prosthetic device 600 that includes a body 602 with both guide tubes 606 passing through the body and guide bars 608, 610 mounted medial to the body to help constrain and control the motion of resiliently flexible wires 604. The body 602, wires 604, and guide tubes 606 can be the same or similar to what is described above with reference to FIG. 38.

The device 600 can include both upper bars 608 and lower bars 610. The upper bars 608 are position above the wires 604 just medial to the guide tubes 606 and the lower bars 610 are positioned below the wires 604 just medial to the guide tubes. The bars 608, 610 can provide and upward and downward limiter to the wires 604 to further direct and control the bulging motion of the wires between the bars. No stops are shown on the wires in FIG. 39, though in other embodiments, stops can be included on the wires 604 just medial to the bars 608, 610 to limit the motion of the wires laterally between the bars and/or through the guide tubes when the user opens his jaws and the wires relax.

In any of the disclosed embodiments, the disclosed resiliently deformable wires can comprise any cross-sectional shape, such as circular, elliptical, polygonal, flattened strips, etc. Further, the "wires" can comprise any resiliently deformable material, metallic materials, polymeric materials, and/or other non-metallic materials, and the wires can have elastic and/or superelastic deformation properties. Shape-memory materials, such as Nitinol, are exemplary materials that can be used for the wires.

In any of the disclosed embodiments, the construction can be flipped with the lower jaw portion or anchor portion attaches to the patient's upper dental arch and the tongue portion or bulging portion protrudes down toward the patient's native tongue to assist the tongue's functionality.

In any of the disclosed embodiments, the lower jaw portion and/or the upper jaw contacts or upper jaw portion can comprise a relatively softer layer of material that contacts the native anatomy of the mouth and a relatively harder layer of material that provides rigidity and supports the wires and other components of the prosthesis. The softer layer of material can protect the patients teeth, gums, and/or palate tissue and can also be a removable and replaceable layer such that that the softer layer can be replaced when it becomes worn, can be replaced for sanitary purposes, and/or can be replaced to provide a new layer of adhesive or other engagement mechanism.

In some embodiments, the prosthesis can be used primarily for assistance with eating and/or swallowing. For example, the patient can insert the prosthesis into the mouth prior to eating, and then remove the prosthesis after eating. In other embodiments, the prosthesis can be configured to be more permanently installed in the patient's mouth yet still readily removable, like a denture or dental retainer. In other embodiments, the prosthesis can be surgically implanted in the patient's mouth for long term use, such as by suturing to tissue or mechanically connecting to the teeth or dental implants. In embodiments that are configured to be removed from and reinserted into the mouth by the patient, the prosthesis can be partially disassembled for cleaning, adjusting, and/or replacing components. Thus, this technology can serve to enhance swallowing rehabilitation as a temporary aid and can be used to permanently replace lost tongue functionality.

In exemplary diagnosis and/or treatment methods, a swallowing evaluation (e.g., bedside or radiographic) can performed on a patient, and after the swallowing evaluation, if significant oral/oropharyngeal dysfunction exists the patient may be considered for an intra-oral prosthesis as disclosed herein. This can involve close observation by physician and/or a speech language pathologist. Patients considered for the disclosed intra-oral prostheses may be evaluated for safety (e.g., regarding risk of aspiration). In some short-term treatments, the patient may receive use the disclosed technology as a result of an acute illness while oropharyngeal muscle strength has decreased (e.g., sarcopenia).

Alternatively, especially in patients with partial tongue or pharynx resection or radiation associated dysfunction, the disclosed prostheses may be used for long-term rehabilitation. In some cases, the prosthesis may only be worn during mealtime, though in other cases it could be worn during daytime hours and removed at night, depending on patient comfort and preference.

The prostheses disclosed herein can help a patient with speaking, drinking, swallowing, chewing, breathing, and/or various other functions typically associated with a native tongue.

The technology disclosed herein with regarding intra-oral prostheses can also be applied to other anatomical prostheses. The use of one muscle group to compress a resiliently deformable and/or superelastic framework allows the outbulging of the framework in a vector that may replace a debilitated second muscle group or amputated extremity. The use of this technology is described elsewhere herein in the realm of intra-oral prostheses and dysphagia, using the muscles of mastication to compress a latticework tongue portion and provide bulk and pressure in the vector of a weak or absent tongue. Similarly, this mechanism can be used to replace the function of other debilitated or amputated body parts, such as fingers, toes, hands, feet, or other extremities. Benefit of using this technology to replace the function of debilitated or amputated body parts include that it can provide a very slim profile and sturdy mechanical design. One exemplary embodiment of this technology with respect to the extremities is a biomechanically powered glove/shoe, or prosthetic hand/foot, or digit device. Digit motion can be be driven by a specially designed array of superelastic metal wires, or other resiliently deformable wires, contained within hollow guide tubing. Such a prosthetic limb/digit device can be lightweight and low profile. Unlike other extremity prosthetics that may rely on the thermally induced phase transformation of superelastic alloys, such as Nitinol, extremity prosthetics employing the disclosed technology can rely on efficient mechanical design and shape memory properties of superelastic alloys to yoke the strength of adjacent muscles to augment or power the prosthetic replacement of an amputated or dysfunctional extremity. With respect to the hands and fingers, the superelastic wires can be fixed at the distal phalanges of the normally functioning fingers. When the hand closes, excess wire can be pushed through the guide tubes into a latticework portion that pulls the prosthetic fingers into a flexed position. Adjustments can be made to allow fine grasp of prosthetic index and thumb digits. Such prostheses can allow for grasping of all digits, prosthetic and native, in a coordinated motion.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Any of the features or characteristics described herein in relation to any one or more of the described embodiments can also be used with or included in any of the other described embodiments where possible, even if such features or technologies are not specifically mentioned in direct connection to a specific embodiment.

Features, integers, characteristics, compounds, materials, or other features described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope and spirit of these claims.

The invention claimed is:

1. An intra-oral prosthesis, comprising:
    an anchor portion configured to anchor the prosthesis intra-orally to a patient's lower jaw or to the patient's upper jaw;
    a tongue portion coupled to the anchor portion and comprising a flexible portion comprising flexible wires, wherein the tongue portion is configured such that, when the patient closes the patient's jaws with the intra-oral prosthesis in the patient's mouth:
        the tongue portion resiliently deforms upwardly relative to the anchor portion toward the patient's upper jaw to simulate movement of the native tongue during swallowing, or the tongue portion resiliently deforms downwardly relative to the anchor portion toward the patient's lower jaw to cooperate with the native tongue during swallowing;

guide tubes coupled to, or formed in, the anchor portion, such that at least some of the flexible wires extend through the guide tubes; and an actuation portion configured to contact the patient's upper jaw if the anchor portion is anchored to the patient's lower jaw, or configured to contact the patient's lower jaw if the anchor portion is anchored to the patient's upper jaw, the actuation portion being coupled to ends of the wires that extend through the guide tubes, and wherein when the patient articulates the patient's lower jaw toward the patient's upper jaw, the actuation portion of the prosthesis moves relatively toward the anchor portion of the prosthesis, which pushes the wires through the guide tubes and causes the tongue portion to bulge relative to the anchor portion.

2. The intra-oral prosthesis of claim 1, wherein the flexible wires form a lattice or mesh.

3. The intra-oral prosthesis of claim 1, wherein the actuation portion comprises a layer of flexible material that arches over the flexible wires and is secured to the anchor portion.

4. The intra-oral prosthesis of claim 1, wherein the prosthesis further comprises at least one biasing member to bias the anchor portion apart from the actuation portion.

5. The intra-oral prosthesis of claim 1, wherein the tongue portion comprises a sheet of flexible material that covers the flexible portion and forms a continuous contact surface of the tongue portion for engaging food within the mouth.

6. The intra-oral prosthesis of claim 5, wherein the sheet of flexible material is removably coupled to the anchor portion such that the sheet can be readily detached from the prosthesis and reattached to the prosthesis.

7. The intra-oral prosthesis of claim 5, wherein the tongue portion comprises a semi-rigid mass positioned between the flexible wires and the sheet of flexible material, the semi-rigid mass configured to shape the sheet to simulate a shape of a native tongue.

8. The intra-oral prosthesis of claim 1, wherein the anchor portion has an arcuate shape and secures the prosthesis to the patient's lower dental arch or to the patient's upper dental arch, and wherein the tongue portion is configured to be positioned in place of, or over, the patient's native tongue and within the patient's lower dental arch.

9. The intra-oral prosthesis of claim 1, wherein the tongue portion has an anterior deformation section and a posterior deformation section, and the anterior and posterior deformation sections can deform relative to the anchor portion independently of each other as the patient closes the patient's jaws.

10. The intra-oral prosthesis of claim 9, wherein the tongue portion also has a middle deformation section between the anterior and posterior deformation sections, and the middle deformation section can deform relative to the anchor portion independently of the posterior and anterior deformation sections as the patient closes the patient's jaws.

11. A method of using an intra-oral prosthesis, the method comprising:
inserting an intra-oral prosthesis into a patient's mouth, the patient having a lower jaw, an upper jaw, a lower dental arch, and an upper dental arch;
anchoring an anchor portion of the prosthesis to the patient's lower or upper dental arch;
positioning an actuation portion of the prosthesis against a surface of whichever of the patient's lower jaw or the patient's upper jaw that is opposite from the anchor portion; and
closing the patient's jaws to cause the anchor portion and the actuation portion to move toward each other and thereby compress a tongue portion of the prosthesis such that the tongue portion bulges from the anchor portion generally toward the actuation portion to simulate movement of a native tongue during swallowing or to cooperate with the native tongue during swallowing;
wherein the tongue portion comprises a lattice of wires that bulge relative to the anchor portion toward the actuation portion when the actuation portion moves toward the anchor portion; and
wherein closing the patient's jaws causes the wires to slide through guide tubes of the prosthesis to direct the motion of the wires.

12. The method of claim 11, wherein anchoring the anchor portion of the prosthesis to the patient's lower or upper dental arch comprises temporarily positioning the anchor portion over the patient's lower or upper dental arch to assist with swallowing while the patient eats, and the method further comprises removing the prosthesis from the patient's mouth after eating.

13. The method of claim 11, wherein positioning the actuation portion of the prosthesis against a surface of the patient's mouth comprises positioning two or more discrete contact pads of the prosthesis at two or more discrete locations in the patient's mouth opposite the anchor portion.

14. An intra-oral prosthesis, comprising:
an anchor portion configured to anchor the prosthesis intra-orally to a patient's lower jaw or to the patient's upper jaw; and
a tongue portion coupled to the anchor portion and comprising a flexible portion configured such that, when the patient closes the patient's jaws with the intra-oral prosthesis in the patient's mouth:
the tongue portion resiliently deforms upwardly relative to the anchor portion toward the patient's upper jaw to simulate movement of the native tongue during swallowing, or
the tongue portion resiliently deforms downwardly relative to the anchor portion toward the patient's lower jaw to cooperate with the native tongue during swallowing;
wherein the tongue portion comprises a sheet of flexible material that covers the flexible portion and forms a continuous contact surface of the tongue portion for engaging food within the mouth; and
wherein the tongue portion comprises a semi-rigid mass positioned between the flexible wires and the sheet of flexible material, the semi-rigid mass configured to shape the sheet to simulate a shape of a native tongue.

15. The intra-oral prosthesis of claim 14, wherein the flexible portion comprises flexible wires.

16. The intra-oral prosthesis of claim 15, wherein the flexible wires form a lattice or mesh.

17. The intra-oral prosthesis of claim 15, further comprising guide tubes coupled to, or formed in, the anchor portion, such that at least some of the flexible wires extend through the guide tubes.

18. The intra-oral prosthesis of claim 14, wherein the sheet of flexible material is removably coupled to the anchor portion such that the sheet can be readily detached from the prosthesis and reattached to the prosthesis.

19. The intra-oral prosthesis of claim 14, wherein the anchor portion has an arcuate shape and secures the prosthesis to the patient's lower dental arch or to the patient's upper dental arch, and wherein the tongue portion is configured to be positioned in place of, or over, the patient's native tongue and within the patient's lower dental arch.

20. The intra-oral prosthesis of claim 14, wherein the tongue portion has an anterior deformation section and a posterior deformation section, and the anterior and posterior deformation sections can deform relative to the anchor portion independently of each other as the patient closes the patient's jaws.

21. The intra-oral prosthesis of claim 20, wherein the tongue portion also has a middle deformation section between the anterior and posterior deformation sections, and the middle deformation section can deform relative to the anchor portion independently of the posterior and anterior deformation sections as the patient closes the patient's jaws.

\* \* \* \* \*